(12) United States Patent
Feemster et al.

(10) Patent No.: US 8,728,140 B2
(45) Date of Patent: May 20, 2014

(54) THERAPEUTIC INTRA-VAGINAL DEVICES AND METHODS

(76) Inventors: Stacy Lee Feemster, Capitola, CA (US); Terry Wayne Alsberg, Capitola, CA (US)

( * ) Notice: Subject to any disclaimer, the term of this patent is extended or adjusted under 35 U.S.C. 154(b) by 1144 days.

(21) Appl. No.: 11/935,620

(22) Filed: Nov. 6, 2007

(65) Prior Publication Data

US 2008/0125692 A1 May 29, 2008

Related U.S. Application Data

(60) Provisional application No. 60/864,506, filed on Nov. 6, 2006.

(51) Int. Cl.
*A61F 7/12* (2006.01)
*A61F 7/00* (2006.01)

(52) U.S. Cl.
USPC .............................................. 607/113; 607/96

(58) Field of Classification Search
USPC ...................... 607/96–99, 113; 128/830–841
See application file for complete search history.

(56) References Cited

U.S. PATENT DOCUMENTS

| | | | |
|---|---|---|---|
| 2,069,284 A | 2/1937 | Solomon | |
| 2,184,642 A | 12/1939 | Glass | |
| 2,192,768 A | 3/1940 | Cross | |
| 3,117,573 A | 1/1964 | Snell | |
| 3,170,465 A * | 2/1965 | Henney et al. | 607/113 |
| 3,952,737 A | 4/1976 | Lipfert et al. | |
| 4,320,751 A | 3/1982 | Loeb | |
| 4,381,771 A | 5/1983 | Gabbay | |
| 4,428,370 A | 1/1984 | Keely | |
| 4,486,191 A | 12/1984 | Jacob | |
| 4,770,167 A * | 9/1988 | Kaali et al. | 128/832 |
| 4,907,589 A * | 3/1990 | Cosman | 606/34 |
| 4,989,618 A | 2/1991 | Shihata | |
| 5,069,906 A | 12/1991 | Cohen et al. | |
| 6,186,973 B1 | 2/2001 | Buzot | |
| 6,418,930 B1 * | 7/2002 | Fowler | 128/830 |
| 6,526,980 B1 * | 3/2003 | Tracy et al. | 128/830 |
| 6,558,381 B2 | 5/2003 | Ingle et al. | |
| 6,629,535 B2 | 10/2003 | Ingle et al. | |
| 6,741,895 B1 | 5/2004 | Gafni et al. | |
| 6,749,624 B2 | 6/2004 | Knowlton | |
| 7,044,928 B2 | 5/2006 | LeMay et al. | |

(Continued)

FOREIGN PATENT DOCUMENTS

| | | | | |
|---|---|---|---|---|
| CN | 1617689 A | | 5/2005 | |
| GB | 2069336 A | | 8/1981 | |
| RU | 2218130 | * | 12/2003 | A61F 7/00 |

OTHER PUBLICATIONS

First Office Action for Chinese Patent Application No. 200780047235.4, Dec. 16, 2010, 9 pages.

(Continued)

*Primary Examiner* — Linda Dvorak
*Assistant Examiner* — Adam Avigan
(74) *Attorney, Agent, or Firm* — Fenwick & West LLP

(57) ABSTRACT

Intra-vaginal devices and methods are disclosed for a broad range of applications in the women's health field. The devices and methods provide for placement in the cervical region, and for transferring heat to a cervical region, a barrier contraception method, collection of menstrual fluid, and release of drugs and/or hormones intra-vaginally. The device also can address multiple women's health issues.

14 Claims, 22 Drawing Sheets

(56) References Cited

U.S. PATENT DOCUMENTS

| | | | |
|---|---|---|---|
| 2001/0039391 A1* | 11/2001 | Augustine | 602/2 |
| 2004/0186535 A1 | 9/2004 | Knowlton | |
| 2005/0171525 A1* | 8/2005 | Rioux et al. | 606/41 |
| 2005/0192652 A1* | 9/2005 | Cioanta et al. | 607/105 |
| 2007/0021809 A1 | 1/2007 | Cole et al. | |

OTHER PUBLICATIONS

"Welcome to Diva International," DivaCup®, 2005, [online] [Retrieved on Feb. 15, 2008] Retrieved from the Internet <URL: http://divacup.com/>.

"Instead", Oochi, [online] [Retrieved on Feb. 15, 2008] Retrieved from the Internet <URL: http://oochi.biz/instead/public/>.

"Introducing the Moon Cup ®, identical to The Keeper but made from medical-grade silicone, for all women, especially for those with an allergy to latex rubber," The Keeper®, Inc., 2006, [online] [Retrieved on Feb. 19, 2008] Retrieved from the Internet <URL: http://keeper.com/index.html>.

"About NuvaRing," NuvaRing, [online] [Retrieved on Feb. 19, 2008] Retrieved from the Internet <URL: http://www.nuvaring.com/Consumer/switch/aboutNuvaRing/index_flash.asp?guid={4976C54A-88FE-4E48-A42D-A613E3303254}&sid=792598798>.

"A Vibrating tampon to relieve menstrual cramps," vBulletin® v3.6.8, 2000-2008, [Retrieved on Feb. 15, 2008] Retrieved from the Internet <URL: http://www.atforumz.com/archive/index.php/t-148980.html>.

Cornforth, T., "Dysmenorrhea—What You Need to Know About Menstrual Cramps," About.com: Women's Health, [online] [Retrieved on Nov. 6, 2006] Retrieved from the Internet <URL: http://womenshealth.about.com/cs/crampsmenstrual/a/dysmenorrheacr.htm>.

"Cervix," Wikipedia, Feb. 11, 2008, [Retrieved on Feb. 19, 2008] Retrieved from the Internet <URL:http://en.wikipedia.org/wiki/Cervix>.

Akin, M. et al, "Continuous Low-level, Topical Heat Wrap Therapy as Compared to Acetaminophen for Primary Dysmenorrhea," The Journal of Reproductive Medicine, Sep. 2004, pp. 739-745, vol. 49, No. 9.

Akin, M. et al, "Continuous Low-level, Topical Heat in the Treatment of Dysmenorrhea," Obstetrics & Gynecology, Mar. 2001, pp. 343-349, vol. 97, No. 3.

"Frustum", Wikipedia, Jan. 29, 2008, [online] [Retrieved on Feb. 14, 2008] Retrieved from the Internet <URL: http://en.wikipedia.org/wiki/Frustum>.

Weisstein, E.W., "Conical Frustum," MathWorld—A Wolfram Web Resource, 1999-2008, [online] [Retrieved on Feb. 14, 2008] Retrieved from the Internet <URL:http://mathworld.wolfram.com/ConicalFrustum.html>.

"Moment: Physics," Wikipedia, Feb. 19, 2008, [online] [Retrieved on Feb. 19, 2008] Retrieved from the Internet <URL: http://en.wikipedia.org/wiki/Moment_(physics)>.

PCT International Search Report and Written Opinion, PCT/US07/083816, Aug. 7, 2008.

European Patent Office, Communication Pursuant to Article 94(3) EPC, European Patent Application No. 07 863 990.3, Nov. 5, 2012, 4 Pages.

Notification of Second Office Action for Chinese Patent Application No. 200780047235.4, mailed on Feb. 1, 2012, 7 Pages.

Supplementary European Search Report mailed Jan. 9, 2012, European Patent Application No. EP07863990.3, 5 pages.

Chinese Third Office Action, Chinese Application No. 200780047235.4, May 9, 2012, 8 pages.

Summons to attend oral proceeding pursuant to Rule 115(1) EPC, European Patent Application No. EP 07863990.3, Jun. 7, 2013, 3 Pages.

* cited by examiner

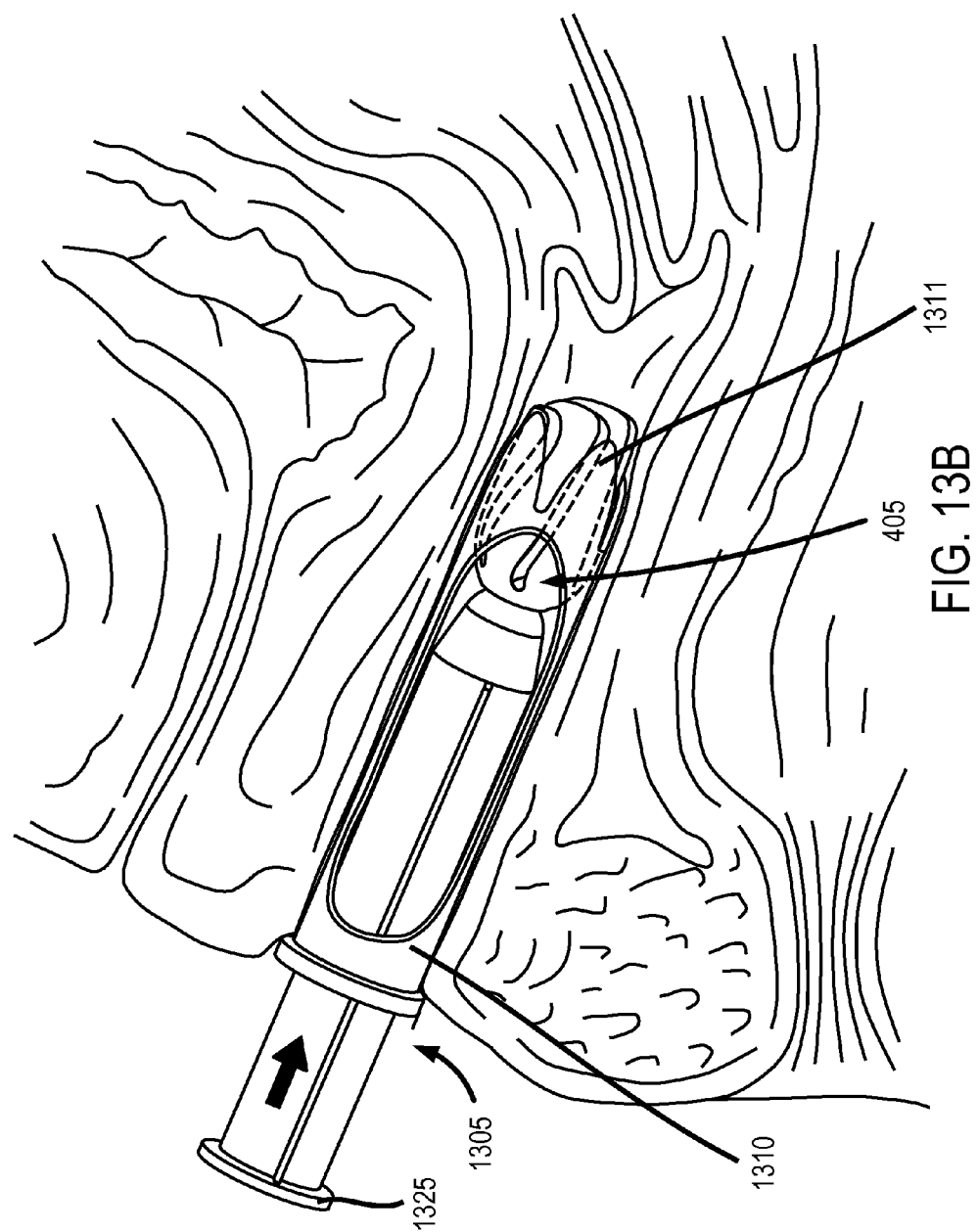

THERAPEUTIC INTRA-VAGINAL DEVICES AND METHODS

RELATED APPLICATIONS

This application: claims priority under 35 U.S.C. §119(e) to U.S. patent application Ser. No. 60/864,506, filed on Nov. 6, 2006, entitled "Device and Method for Amelioration of Dysmenorrhea," which is incorporated herein in its entirety by reference.

BACKGROUND

The present invention relates to intra-vaginal devices, and more specifically, to intra-vaginal devices and methods for providing therapeutic treatment to the cervical region.

Women's personal health products, including feminine hygiene products, reproductive health products, and other women's health products, have seen relatively little progress in the past fifty years. Women looking for solutions to today's myriad feminine health issues traditionally have turned to the same antiquated devices and techniques as generations before them.

For relief from dysmenorrhea, for example, women typically turn to either chemical means, i.e., pain relief medications, hormones, or application of external heat to the pelvic region. These relief options tend to provide inadequate effectiveness, and are associated with other disadvantages such as the visibility of external heat application and the side effects and limitations of hormones and pain relief drugs to provide consistent pain relief for the duration of a woman's menstrual cycle.

For various other women's health issues in which an intra-vaginal device may be used, such as barrier methods of birth control (e.g., diaphragm, cervical cap), insertable chemical contraceptive devices, as well as newer methods of collection of menstrual fluid (e.g., disposable menstrual cups), manual insertion and removal remain the norm. Many women find such manual techniques complicated and unhygienic. Of these, the barrier birth control devices often have additional shortcomings associated with them, such as need for a precise fit and thus medical office fittings for devices made in a variety of sizes. Alternatives to disposable menstrual cups remain limited to tampons and sanitary napkins, products that are often inconvenient, limited to short periods of wear, and/or associated with additional health risks, such as Toxic Shock Syndrome.

SUMMARY

In various embodiments, the present invention provides intra-vaginal devices, as well as methods for use and insertion thereof, with a broad range of applications in the women's health field.

In one embodiment, the present invention provides an intra-vaginal device capable of transferring heat to a cervical region and a method for using the same. The heat thereby transferred is therapeutic, e.g., the heat aids in amelioration of menstrual cramps or other cervical-vaginal discomfort. Uterine cramping is believed to be caused by contraction of the uterine muscles and/or dilation of the cervix, and thus heat applied to the cervical area will have the effect of relaxing the tissues, increasing perfusion, and facilitating dilation. This embodiment of the device of the present invention can take various shapes as described herein. The placement of the device in the cervical region provides direct heat transfer to the cervix uteri and surrounding tissues, providing effective pain relief. In addition, because the device can remain in place for an extended period of time, the device allows for little-to-no interruption in pain relief during a woman's menses. Use of the device is not visible to the outside observer and prevents the need for multiple doses, e.g., of pain-relief drugs or hormone therapies.

In another embodiment, the present invention provides a collapsible intra-vaginal device and insertion method for placement adjacent to a cervix uteri for various women's health applications. The device in this embodiment can be used by women with a range of cervix uteri sizes, and the device and method provide for self-alignment during insertion for correct placement adjacent to the cervix uteri. This embodiment of the device can be used with therapeutic heat as discussed for the above embodiment, as a barrier birth control method (with or without spermicide), for collection of menstrual fluid, and for release of drugs and/or hormones intra-vaginally, as well as for other applications for which proximity to the cervix uteri is important.

In addition to avoiding many of the above-referenced shortcomings of the various prior devices and methods, the present invention allows the ability to address multiple women's health issues with a single device.

The description in the specification is not all inclusive and, in particular, many additional features will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

FIGS. 13A-13B are cut-away side views of insertion of an intra-vaginal device via an insertion device according to one embodiment of the present invention.

One skilled in the art will readily recognize from the following discussion that alternative embodiments of the structures and methods illustrated herein may be employed without departing from the principles of the present invention.

DETAILED DESCRIPTION OF THE EMBODIMENTS

Definitions

The term "adjacent," as used herein is used in it's traditional usage, meaning nearby or close to; proximate. Items that are adjacent may or may not be contiguous (touching).

The term "cervical region," as used herein includes the upper portion of the vagina and the lower portion of the uterus. The "upper portion," according to various embodiments, may be the portion about the midpoint of the vagina, the upper two-thirds (⅔) of the vagina, or within two inches of the cervix. In one embodiment, the cervical region comprises the tissues immediately surrounding the cervix uteri.

The term "dysmenorrhea," as used herein is defined as pain or discomfort experienced just before or during a menstrual period.

The term "frustum," as used herein is defined as the portion of a solid—normally a cone or pyramid—which lies between two parallel planes cutting the solid; each plane section is a base of the frustum.

The term "perfusion," as used here, means fluid flow through an organ or tissue.

The term "therapy," as used herein refers to any useful alteration associated with feminine health, and as used herein includes, but is not limited to, heat therapy, chemical therapy, hormone therapy, birth control, and retention of menstrual fluid.

"Therapeutic heat," as used herein, is heat therapy. In one embodiment, therapeutic heat provides for amelioration of discomfort of the cervical region. In one embodiment, the range of heat that is therapeutic is between 97.0 and 120.0 degrees Fahrenheit. Therapeutic heat, in another embodiment, is the amount of heat transfer required to change the temperature of the cervical region tissues. The heat means may be of various forms, including but not limited to, electric, fluid flow, exothermic chemical reaction, passive, or thermonuclear.

Anatomical Context

Figure 1A:
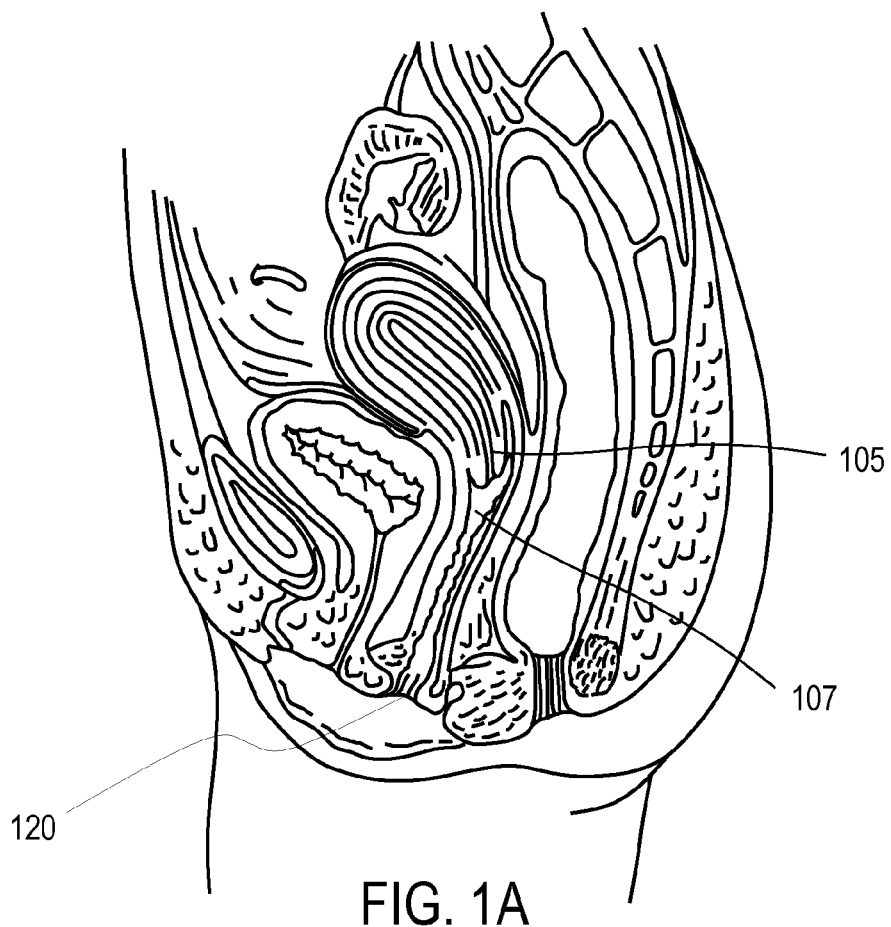
FIGS. 1A and 1B show cross-sectional side and front line drawing views, respectively, of the female reproductive anatomy.
Figure 1B:
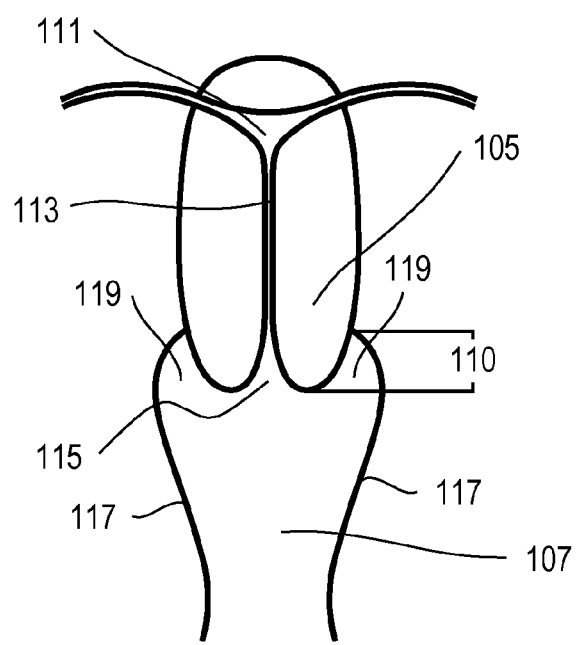

FIGS. 1A and 1B show cross-sectional side and front line drawing views, respectively, of the female reproductive anatomy. As depicted, the portion of the cervix 105 that protrudes into the vagina 107 is the portio vaginalis 110, or ectocervix. The uterus 111 defines fundus 113, which terminates in cervical os 115. The vaginal walls 117 and portio vaginalis 110 define the fornices vaginae, or vaginal fornices 119. As used herein, the cervical region comprises the cervix 105 itself and the surrounding tissues of the uterus 111 and vagina 107. The term cervical, as used herein, refers to aspects of the female anatomy in the cervical region.

The cervix 105 may present itself in various positions with respect to the vaginal canal 107. It is rarely directly aligned with the axis of the vaginal canal 107. As shown in FIG. 1A, e.g., the cervix 105 often is aligned at a slight angle from the axis of the vaginal canal 107 with respect to the vaginal opening 120. The size of the cervix 105 and vagina 107 also may vary greatly from one woman to another. The above-described anatomy thus provides a frame of reference for the devices and methods described herein.

Device Architecture

Figure 2A:
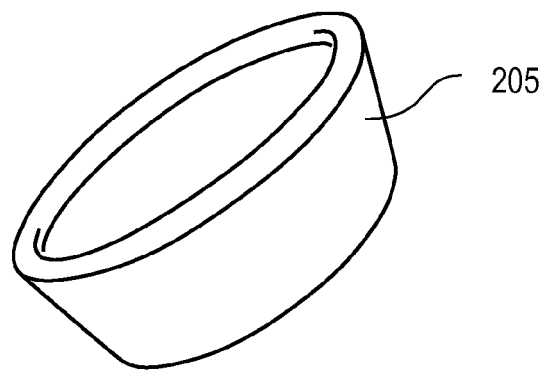
FIGS. 2A, 2B, and 2C are perspective, top view, and cut-away side views of an intra-vaginal device according to one embodiment of the present invention.
Figure 2B:
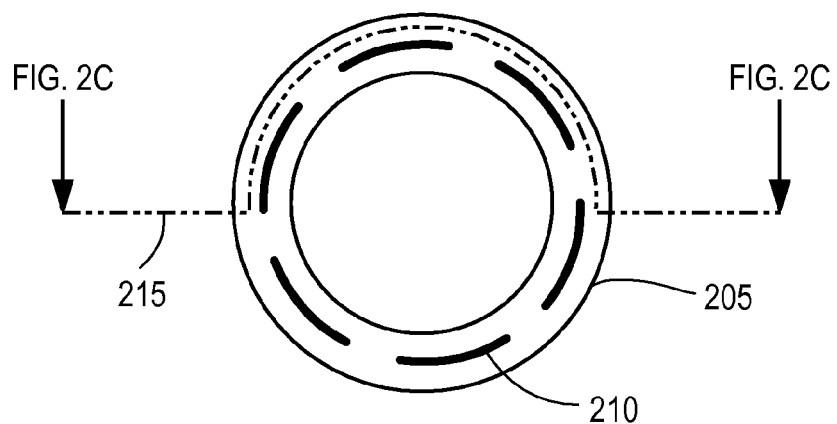
Figure 2C:
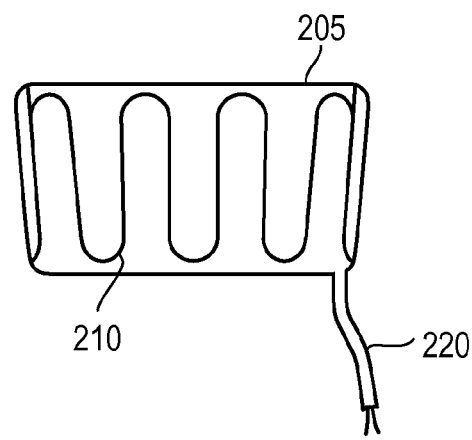

In various embodiments, the present invention provides intra-vaginal devices, as well as methods for use and insertion thereof, with a broad range of applications in the women's health field. FIGS. 2A, 2B, and 2C are perspective, top, and cut-away side views of an intra-vaginal device according to one embodiment of the present invention.

Referring to FIG. 2A, it shows a perspective view of an intra-vaginal device 205 according to one embodiment of the present invention. The embodiment of the device 205 shown in FIGS. 2A-2C is a short, flared, cylindrical ring or hollow inverted conical frustum, however, the device takes other shapes according to various embodiments. The device 205 is designed for placement in the cervical region. The flared cylindrical device 205 shown in FIG. 2A, for example, is of sufficient diameter and length optimized for comfortably surrounding the portio vaginalis 110. The size of the portio vaginalis varies significantly from woman to woman, with the average size being 3 cm in diameter and 2.5 cm in length. A woman's cervix 105 is approximately hemispherical in shape. Thus, the device 205 is shaped in a manner that approximately matches the shape of the cervix 105. The embodiment of the device 205 shown in FIGS. 2A-2C has an open bottom, however, the device 205 bottom may be closed, or solid, in some applications.

Thus, the device 205 in one embodiment comes in a plurality of sizes to accommodate various anatomies, and is comprised of a pliable, elastomeric material so as to allow a relatively small number of sizes to fit a wide variety of women without excessive custom fitting. In other embodiments, the device 205 is made of somewhat more rigid materials, as appropriate for the overall device configuration. The choice of materials, for example, may be determined so as to ease insertion and/or removal of the device 205 in combination with comfort to the user and effectiveness of the intended therapeutic use. In one embodiment, the materials are hypoallergenic. For example, the device 205 may be made of silicone rubber, latex, polyurethane, and various other materials suitable for this purpose. The device 205 is reusable or single-use according to various embodiments. As a result, the materials used for the device 205 may be selected for durability or economy, respectively.

FIG. 2B shows a top view of the device 205 of FIG. 2A. In one embodiment, the device 205 is used in conjunction with a heat source for providing heat to the cervical region. The embodiment in FIGS. 2B and 2C is a device 205 with an electrical heating element 210, depicted as a thick dashed line in the interior of the device 205. A thin dashed line 215 illustrates a cut through the plan view of the device 205; the cut-away side view is shown as FIG. 2C. The electrical heating element 210 is visible in FIG. 2C, which shows a serpentine configuration of the heating element 210. In other embodiments, other heating element 210 configurations are used, e.g., as described below in greater detail in conjunction with FIGS. 9-10E.

Figure 3A:
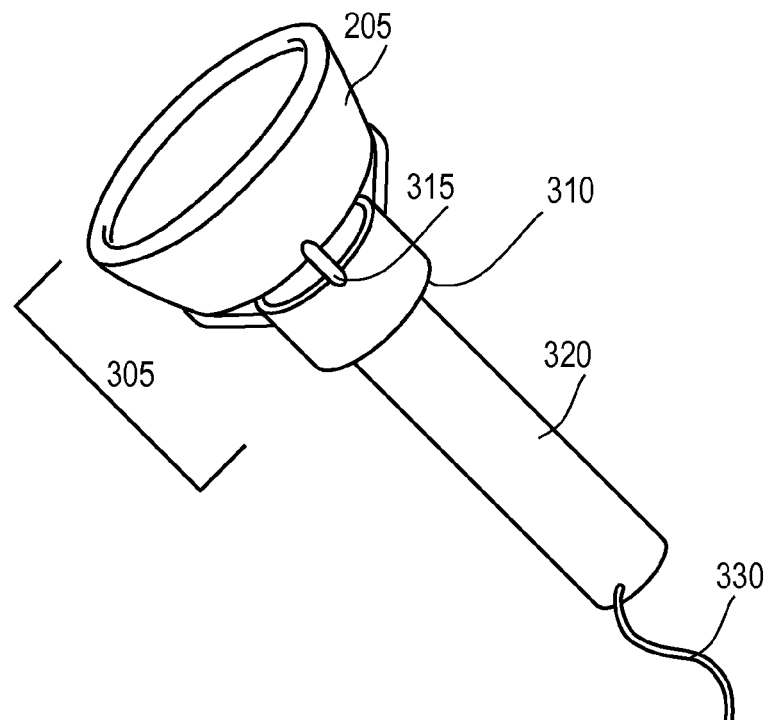
FIG. 3A & 3B are perspective view and cut-away side views of a tampon-based intra-vaginal device according to one embodiment of the present invention.
Figure 3B:
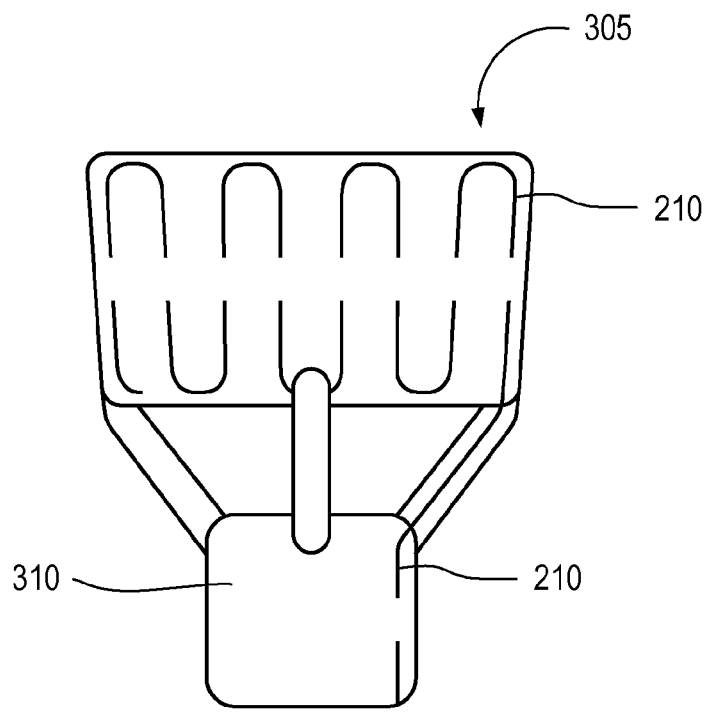

FIG. 3A & 3B are perspective view and cut-away side views of a tampon-based intra-vaginal device 305 according to one embodiment of the present invention.

In one embodiment, the device is used in conjunction with a tampon, and is inserted in conjunction with insertion of a tampon by known methods. An example of a tampon-based device 305 is shown in FIG. 3A. In this embodiment, the top portion of the tampon-based device 305, for placement adjacent to the cervix 105, is similar to the flared cylindrical device 205 described above. However, the tampon-based device 310 additionally has a secondary ring structure 310 that attaches to a standard tampon 320. The secondary ring 315 is separated from the top portion 205 of the device 305 by support members 315 that provide a gap to allow for normal menstrual flow to reach the tampon 320. Removal of the device 310 is in conjunction with the normal removal of the tampon 320 according to one embodiment. The tampon-based device 305 shown is merely one configuration; other embodiments may take a number of other configurations. The tampon-based device 305 may also provide heat as referenced above and discussed in greater detail below. Thus, a heating element 210 is shown in FIG. 3B.

The device 205 shown above may also be used for other applications according to various embodiments, e.g., for menstrual fluid collection, chemical birth control, or barrier method birth control. These applications are described in greater detail in conjunction with FIGS. 4A-4G.

Figure 4A:
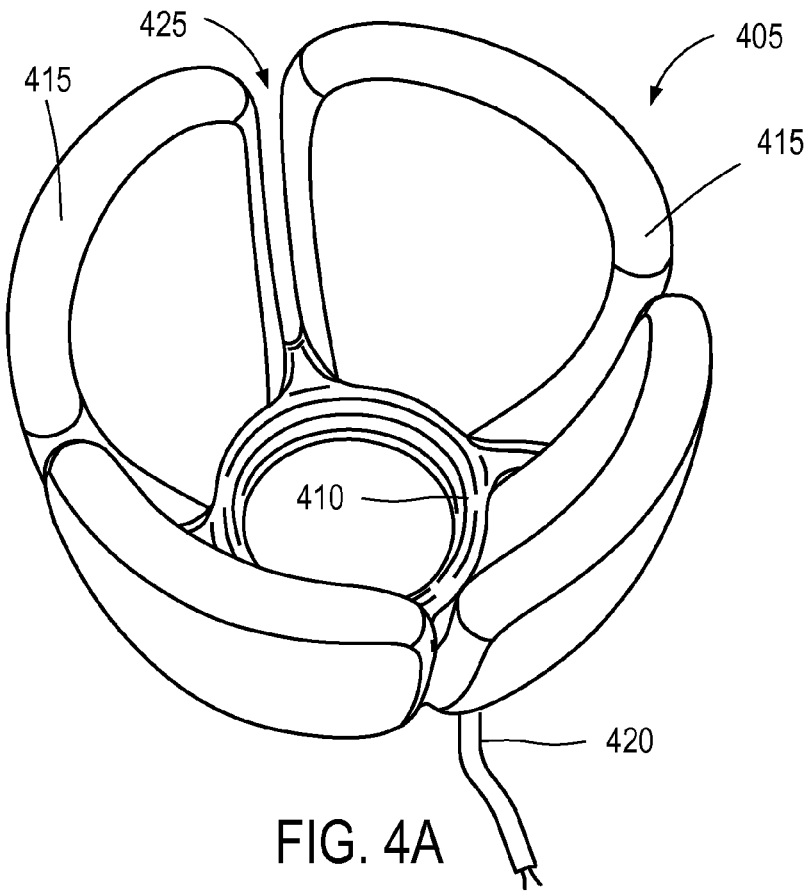
FIGS. 4A & 4B are perspective and cut-away side views of an intra-vaginal device in an expanded configuration according to one embodiment of the present invention.
Figure 4B:
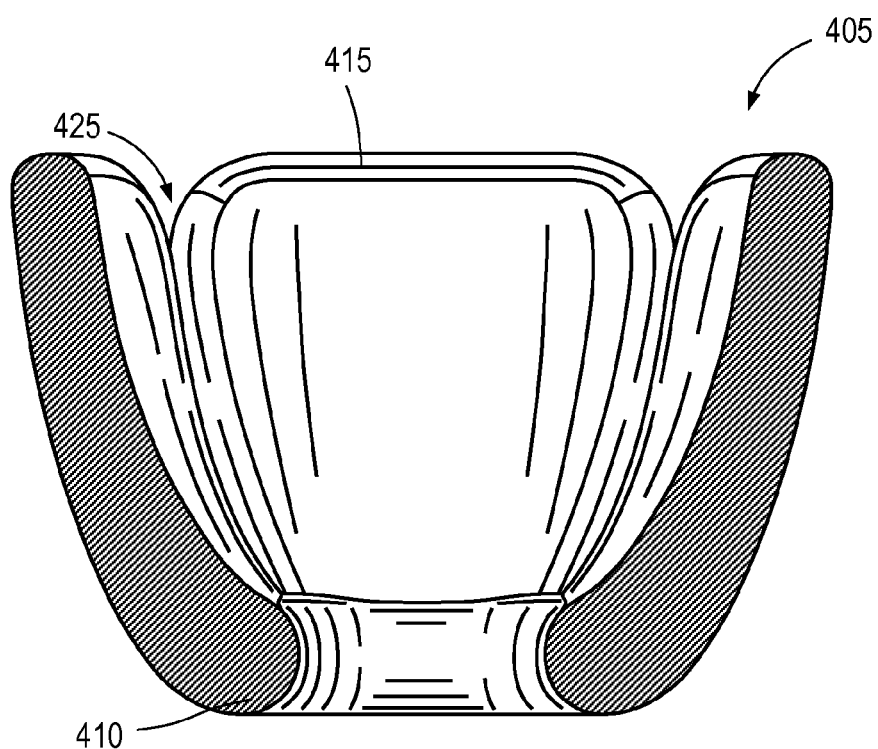

FIGS. 4A & 4B are perspective and cut-away side views of an intra-vaginal device 405 in an expanded configuration according to one embodiment of the present invention. The device 405 is designed for placement in the cervical region, adjacent to a cervix uteri 105. The device 405 has an approximately circular, ring-shaped base 410 and two or more flaps 415 attached at one end to the base 410 according to one embodiment. The depicted device 405 has four (4) flaps 415, however, the device 405 may have more or less than four flaps 415. In the expanded configuration shown in FIGS. 4A and 4B, the flaps 415 together approximate the shape of a hollow inverted frustum, or an open-bottom bowl shape, in one embodiment, with the ring 410 forming the bottom, ring base and the end of the flaps 415 not connected to the ring 410 forming the top base of the frustum. Thus, the device 405 is shaped in a manner that approximately matches the shape of the cervix 105. As shown, the flaps 415 can easily open or close to varying degrees to accommodate a variety of cervix 105 sizes. In some embodiments, the device 405 may have a string, or wire, 420 to aid in removal.

In the embodiment depicted, the area inside the ring 410 is hollow, and thus the device 405 is open. The hole in the ring-shaped base 410 is sufficiently large to allow flow of menstrual and other vaginal fluids to pass through. Slits 425 between the flaps 415 supply an additional pathway for fluid flow.

Figure 4C:
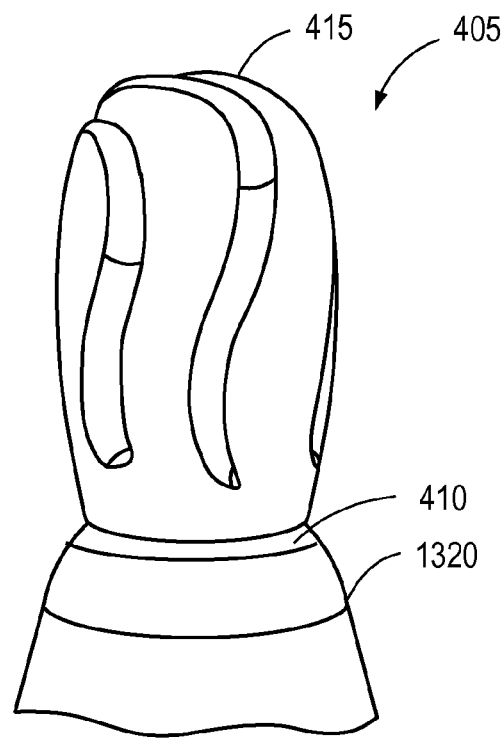
FIGS. 4C & 4D are side and top views of an intra-vaginal device in a collapsed configuration according to one embodiment of the present invention.
Figure 4D:
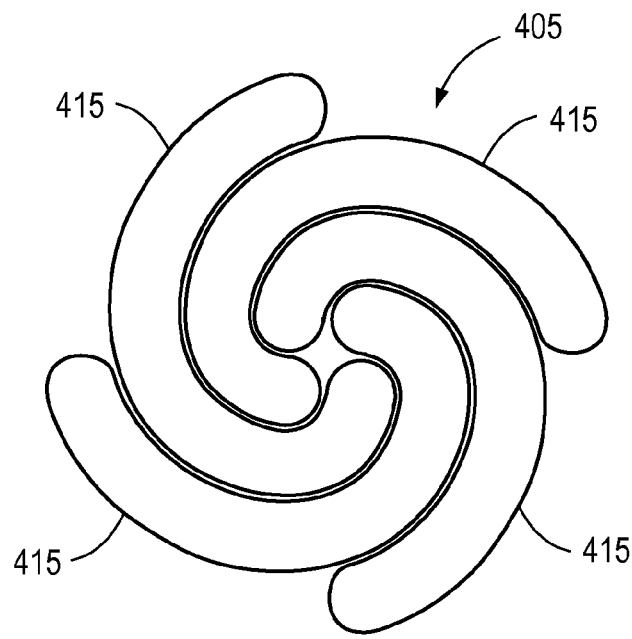

FIGS. 4C & 4D are perspective and top views of an intra-vaginal device 405 in a collapsed configuration according to one embodiment of the present invention. As shown, the flaps 415 can overlap each other in a spiraling fashion to attain a collapsed configuration. In this embodiment, the flaps 415 are tapered towards the edges to facilitate the successive nestling of one flap 415 under the edge of the adjacent flap 415. The overall circumference in the collapsed configuration is sufficiently small to permit the device 405 to fit inside a cylindrical tube for insertion, as described in greater detail in conjunction with FIGS. 13A-13E. In addition, the shape of the upper portion of the device 405 becomes tapered, which facilitates its exit from the cylindrical tube upon insertion. In the collapsed position, the flaps 415 if unconstrained would have sufficient spring force as to tend to open up when the constraint is relieved.

Figure 4E:
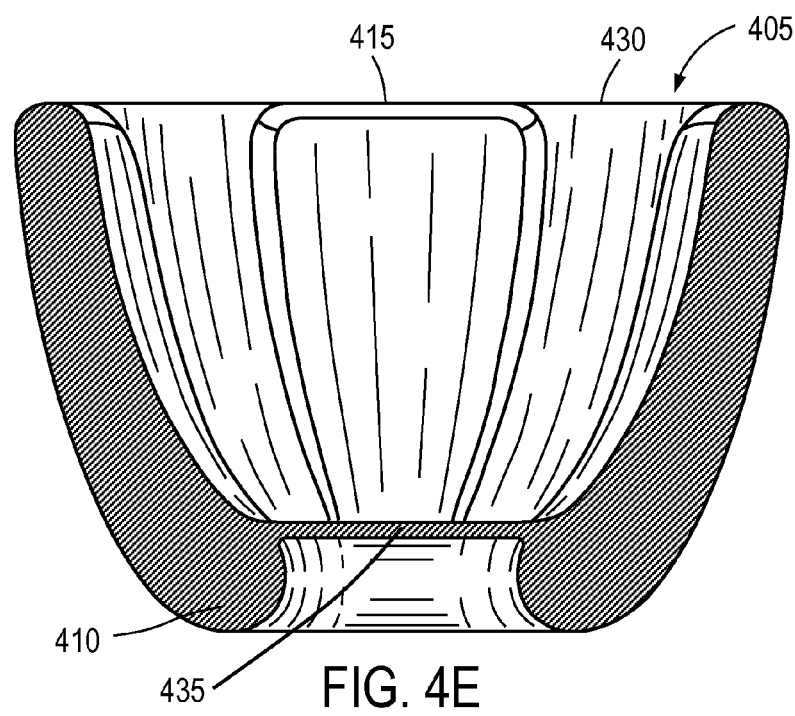
FIGS. 4E & 4F are cut-away side and top views of an intra-vaginal device in a webbed expanded configuration according to one embodiment of the present invention.
Figure 4F:
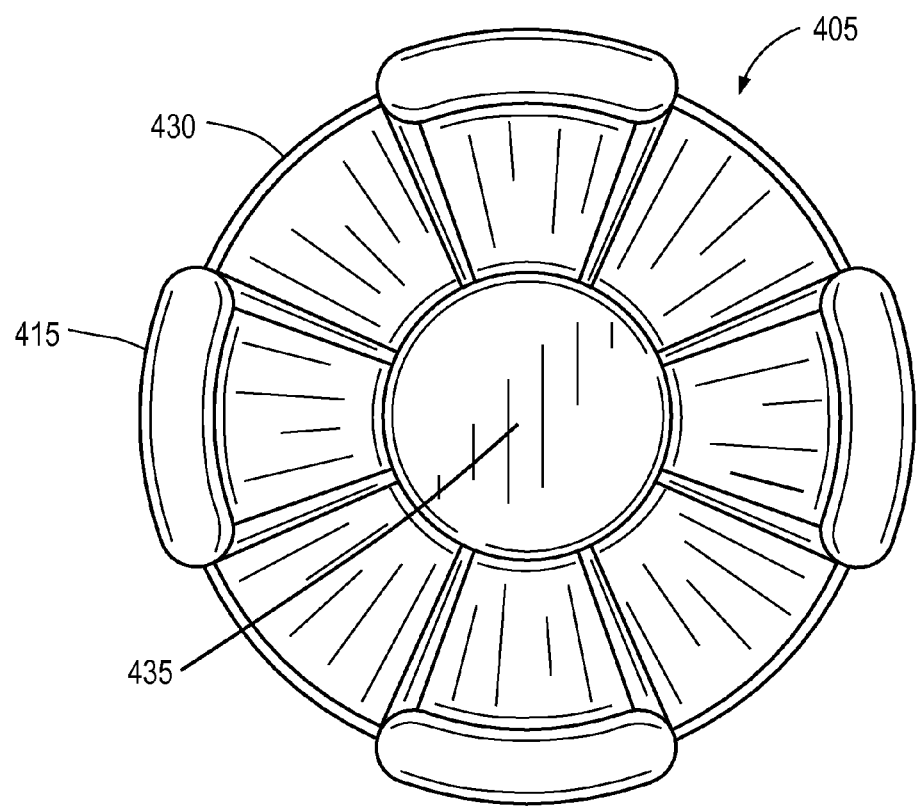
Figure 4G:
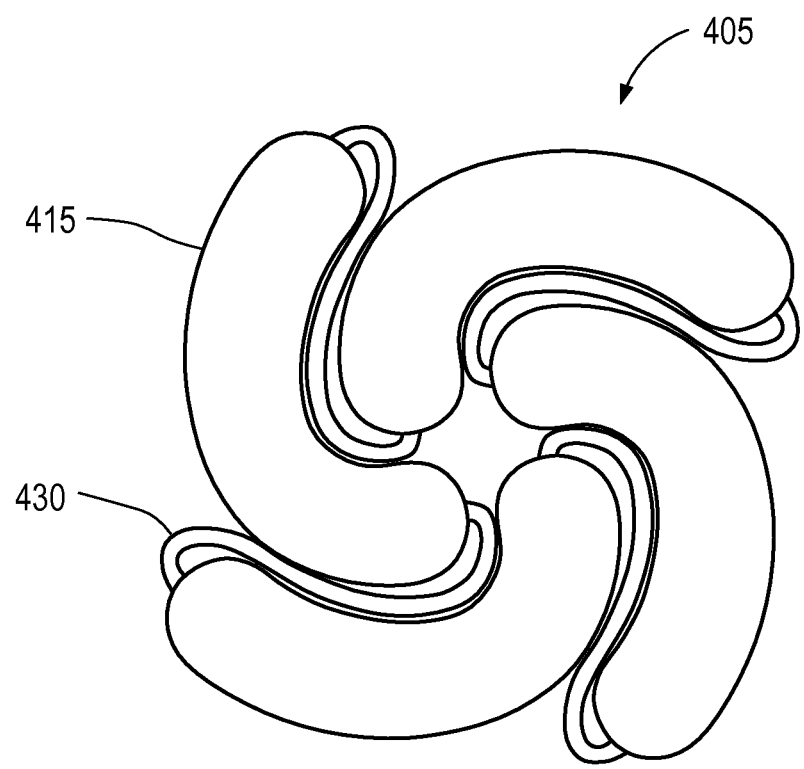
FIG. 4G is a top view of an intra-vaginal device in a webbed collapsed configuration according to one embodiment of the present invention.

FIGS. 4E & 4F are cut-away side and top views of an intra-vaginal device 405 in a webbed expanded configuration according to one embodiment of the present invention, and FIG. 4G is a top view of an intra-vaginal device in a webbed collapsed configuration according to one embodiment of the present invention. The webbed configuration is similar to the configuration described in conjunction with FIGS. 4A-4D, except that the flaps have webbing 430 between them in place of the slits 425, and the area inside the ring base 410 is closed 435, or solid, such that flaps 415 of the device 405 form a continuous structure with no apertures.

Thus, this embodiment of the device 405, once in place, is intended to block the flow of fluids in or out of the os 115 of the cervix 105. For example, the device 405 can act as a barrier to seminal fluid, thereby being suitable as a contraceptive device, or can block, or capture and retain, the flow of menstrual fluids, thereby being an alternative to feminine napkins or tampons for use during menses. The device 405 in this configuration may have addition features for its intended purpose, such as a receptacle for collection of seminal or menstrual fluids, or retention of spermicide. The device 405 may include a string, tab, or other means for retrieval and removal.

According to the embodiment depicted in FIGS. 4A-4G, the device 405 is manufactured out of materials that allow the device 405 to collapse and expand as described above. In one embodiment, the webbing 430 is made of an elastomeric material to allow to stretching of the diameter of the device 405, e.g., if the remainder of the device is not made of an elastomeric material. In another embodiment, the device 405 is manufactured from an elastic, hypoallergenic material as discussed above in conjunction with FIGS. 2A-2C. In these embodiments, the device 405 can accommodate a variety of cervix sizes. The materials for the device 405 should be sufficiently pliable so as to be collapsible, and such that they cause the device 405 to spring open, once inserted, to conform to the vaginal walls 117 without causing injury to those tissues.

Figure 5A:
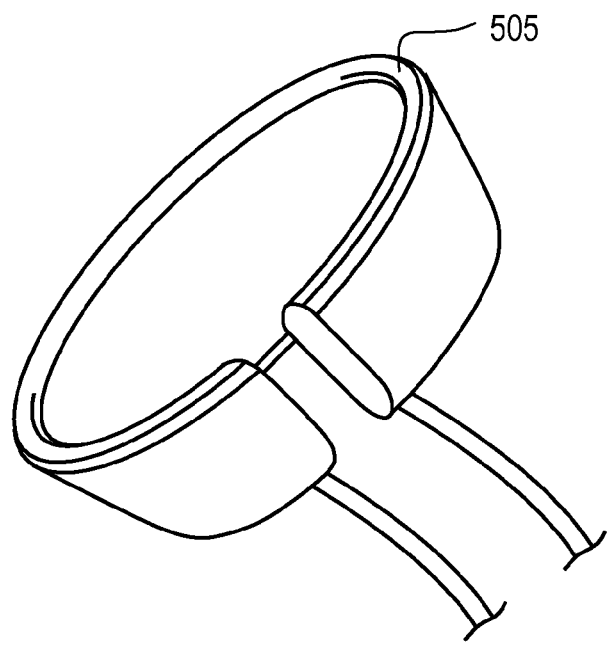
FIGS. 5A & 5B are perspective and side views of a C-shaped intra-vaginal device according to one embodiment of the present invention.
Figure 5B:
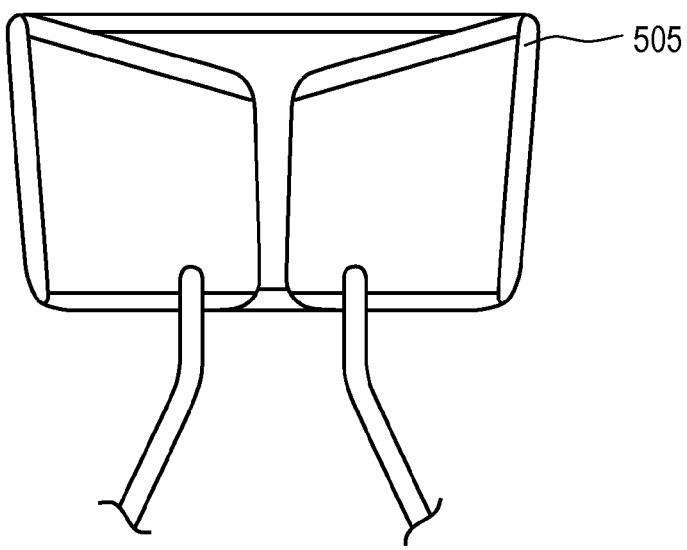

FIGS. 5A & 5B are perspective and side views of a C-shaped intra-vaginal device 505 according to another embodiment of the present invention.

Figure 6:
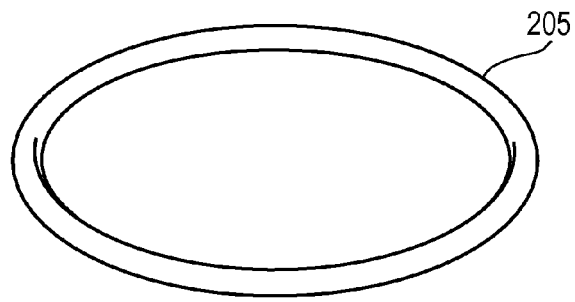
FIG. 6 is a perspective view of a ring-shaped intra-vaginal device according to one embodiment of the present invention.

FIG. 6 is a perspective view of a ring-shaped intra-vaginal device 605 according to one embodiment of the present invention. In this embodiment, the device 605 may include an internal spring similar to that commonly used in a diaphragm, and may be inserted and removed by similar methods.

Figures 7A, 7B:
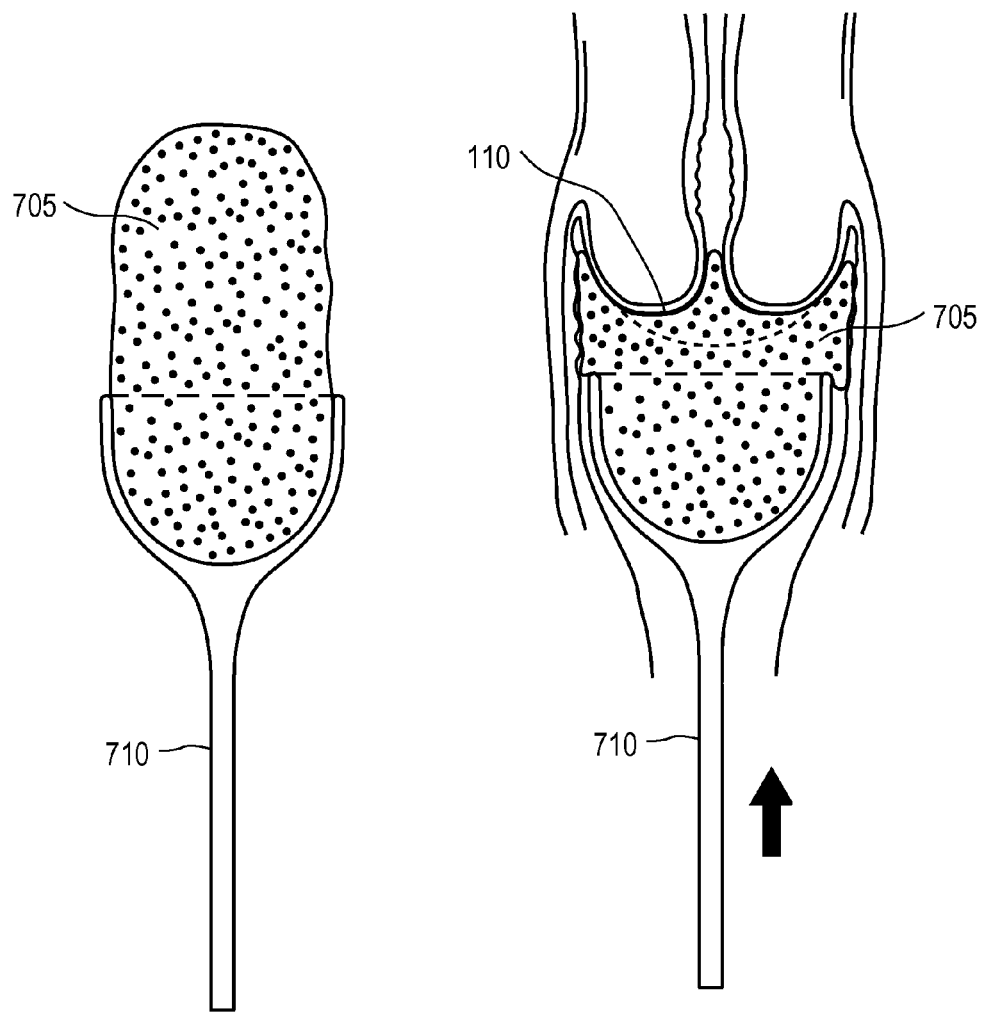
FIGS. 7A and 7B are cut away side views of a gelatinous ball intra-vaginal device according to one embodiment of the present invention.

FIGS. 7A and 7B are cut away side views of a gelatinous ball intra-vaginal device according to one embodiment of the present invention. In this embodiment, the device is comprised of a gelatinous ball 705 or membrane that may take various shapes and sizes. For example, a gelatinous ball 705 may be affixed to a tampon 320 for digital insertion, or may be used in conjunction with an insertion device 710 as shown. As shown, in one embodiment, when the ball 705 is inserted, it conformed to the interior of the cervical region. This device also may include a heating element. These embodiments are merely examples of various configurations the device can take; other configurations are within the scope of the present invention.

Figure 8A:
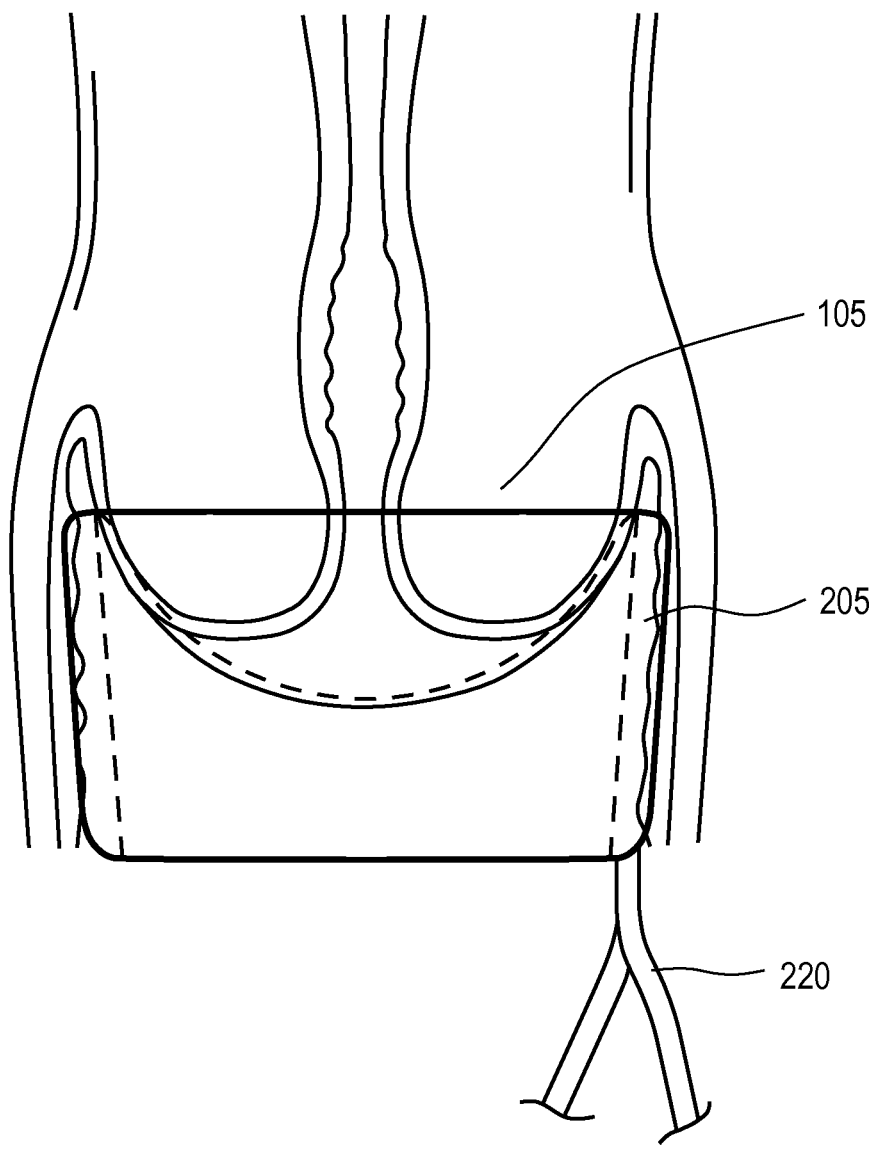
FIGS. 8A-8C are cross-sectional views of three embodiments of inserted intra-vaginal devices according to the present invention.
Figure 8B:
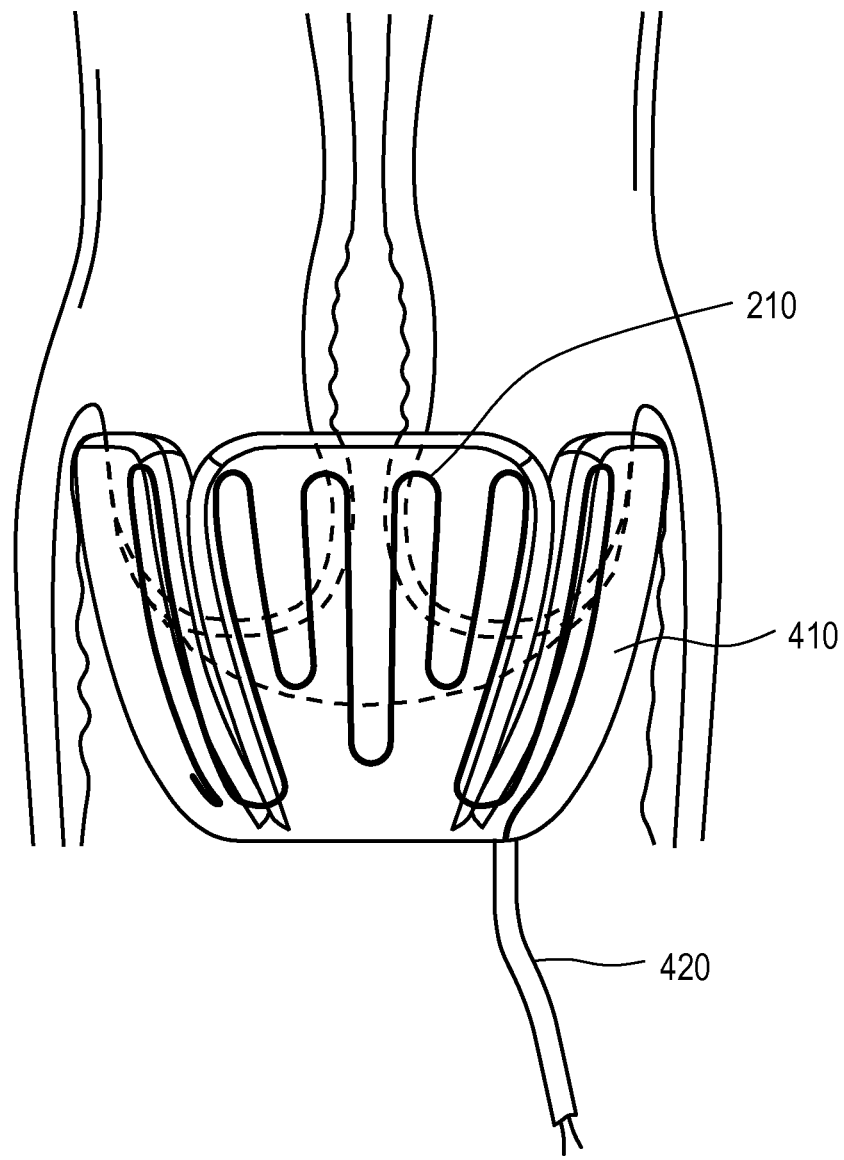
Figure 8C:
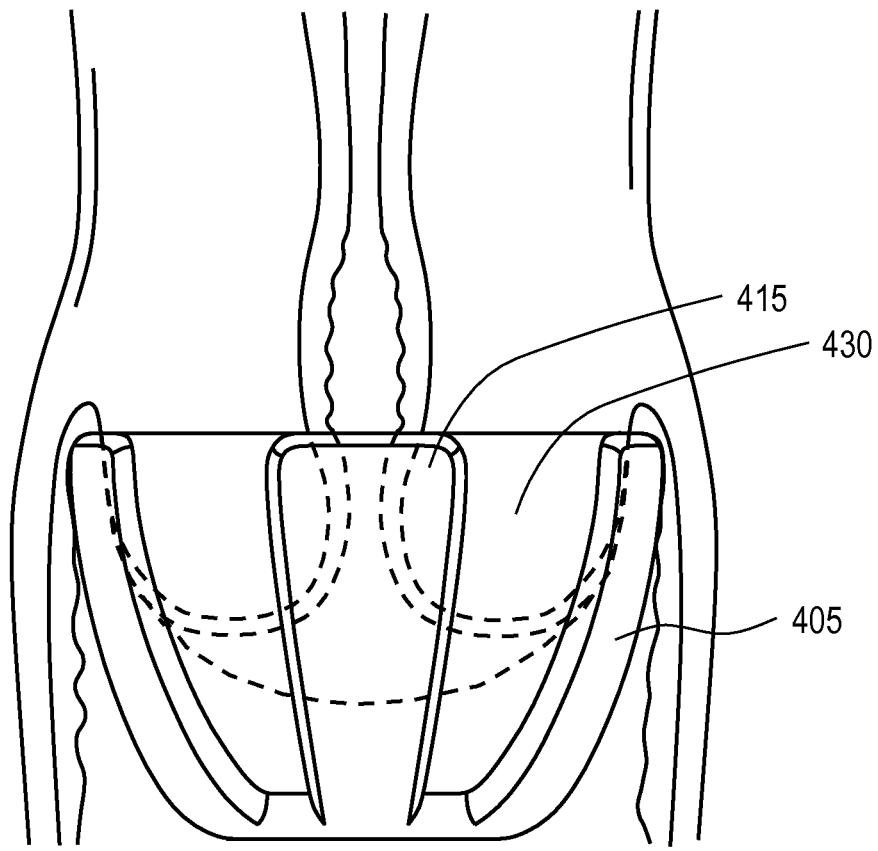

FIGS. 8A-8C are cross-sectional views of three embodiments of inserted intra-vaginal devices according to the present invention. FIG. 8A shows placement of a device 205 closely fitted over the hemispherical cervix 105. Similarly, FIGS. 8B and 8C show placement of a device 405 webbed (FIG. 8C) or not (FIG. 8B) closely fitted over the cervix 105. The devices 205, 405 are placed into the cervical region. In some embodiments, the devices 205, 405 will touch the cervix 105, e.g., when a tight fit is necessary, such as when the device 205, 405 is used as a barrier-type contraceptive. In other embodiments, being within a maximum distance from the cervix 105 is sufficient, e.g., for heat transfer to the cervical and uterine tissues. In one embodiment, when the device 205, 405 is in place, the hollow of the ring base 410 defines an aperture substantially in alignment with the os 115 of the cervix uteri 105.

Therapy

The device 205, 405 described herein is configured for delivering therapy of various types to the cervical region.

One example of a use of the intra-vaginal devices 205, 405 described herein is for providing therapeutic heat to the cervical region. The external application of heat to the uterine/cervical area is a well-known method thought to reduce menstrual cramping. Menstrual cramping, or dysmenorrhea, has been a health challenge to women since the origin of the human species. Studies indicate that dysmenorrhea is caused by uterine contractions and the dilation of the cervix 105 that is required to allow menstrual discharge to pass through the opening. A common remedy for dysmenorrhea has been the application of heat to the abdomen by a variety of methods, e.g., electric heating pads, hot water bottles, or warm baths. These therapies typically have provided limited amelioration and have been supplanted by various drug therapies such as analgesics, muscle relaxers, and various hormone therapies. However, some studies have maintained heat as a superior method of treatment.

The present invention allows heat to be delivered directly to the cervix 105 and surrounding tissues. The device 205, 405 may receive heat by various means. In one embodiment, the device 205, 405 is passively heated. For example, the device 205, 405 may be heated by immersing the device 205, 405 in hot water of a specific temperature range to reach the above-stated temperatures, or heated in a microwave, or by various other heating methods. In this embodiment, the device 205, 405 has sufficient mass per unit volume and high specific heat to allow necessary storage of heat within the device 205, 405. Once sufficiently heated, the device 205, 405 is inserted into position around the portio vaginalis 110, as described above, where its heat is given up to the adjacent tissues. In this embodiment, the device 205, 405 may be reusable, and thus may be reheated.

Figure 9:
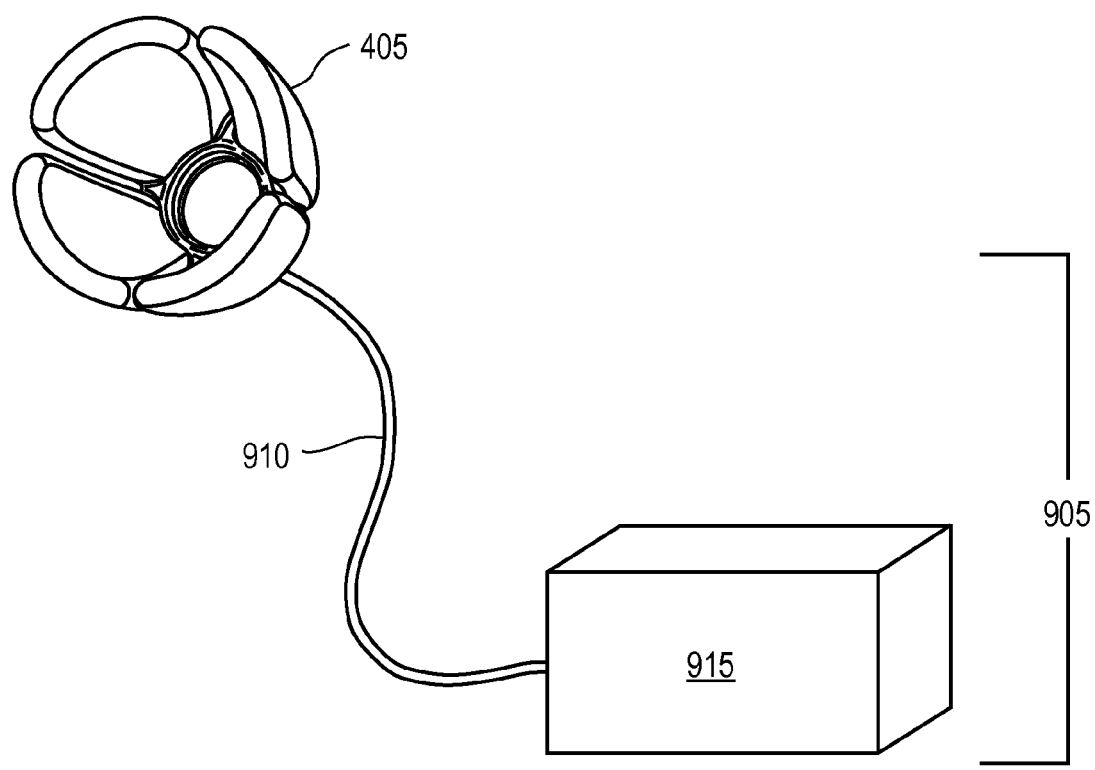
FIG. 9 is a perspective view of an intra-vaginal device in conjunction with a heating apparatus according to one embodiment of the present invention.

FIG. 9 is a perspective view of an intra-vaginal device 205, 405 in conjunction with a heating apparatus 905 according to one embodiment of the present invention. The heating apparatus 905 may be an electric heating means or a fluid flow device heating means according to various embodiments. For example, the apparatus 905 may include wires 910 and a battery pack 915, or tubing 910 and a fluid flow device 915. In an electrical heating embodiment, the device 205, 405 is connected to a battery pack 915 or other electricity source by wires 910. In one embodiment, the device 205, 405 uses a pair of wires wrapped in a single covering 910. The wires 910 are of sufficient length such that the battery pack 915 may be worn externally by the user, and such that battery replacement is possible without removal of the device. In some embodiments, the battery pack 915 may be accompanied by a variable resister or other current regulator (not shown) to more precisely control, either automatically or manually, the temperature supplied to the device 205, 405. Alternatively, the heat source 915 may operate the device 205, 405 via wireless transmission, e.g., via transcutaneous energy transfer according to Faraday's principle.

Referring again to FIG. 9, in a fluid heating embodiment, a device 205, 405 is connected to a fluid flow device 915 by tubing 910. The tubing 910 is of sufficient length such that the fluid flow device 915 may be worn externally by the user. The fluid flow device 915 has the capability of heating the fluid and pumping it around the fluid circuit. In some embodiments, the fluid flow device 915 may include one or more temperature controls to more precisely control the temperature supplied to the device 205, 405.

Figure 10A:
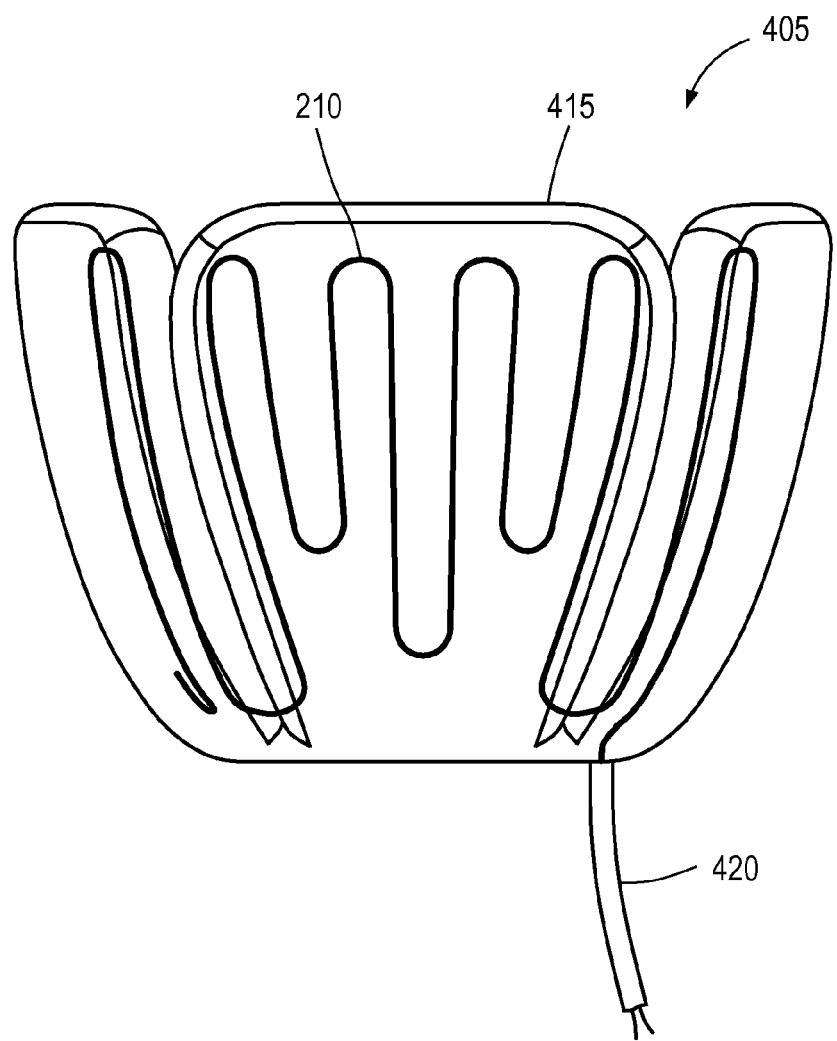
FIGS. 10A-10E are cut-away side views of intra-vaginal devices with various heating elements according to various embodiments of the present invention.
Figure 10B:
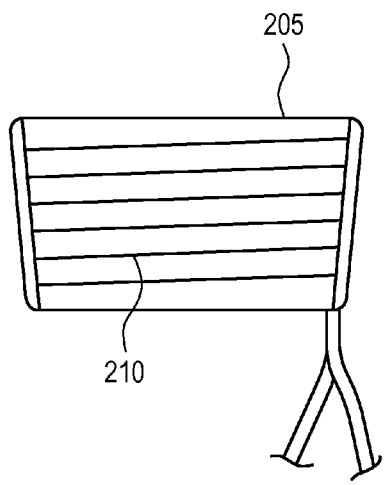
Figure 10C:
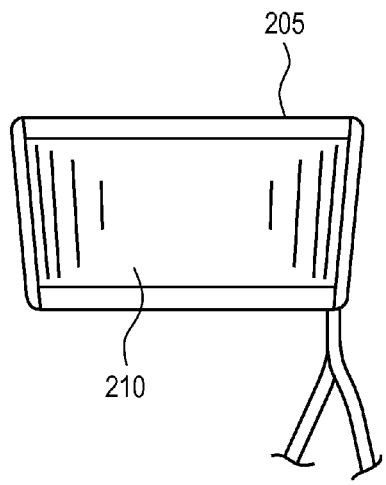
Figure 10D:
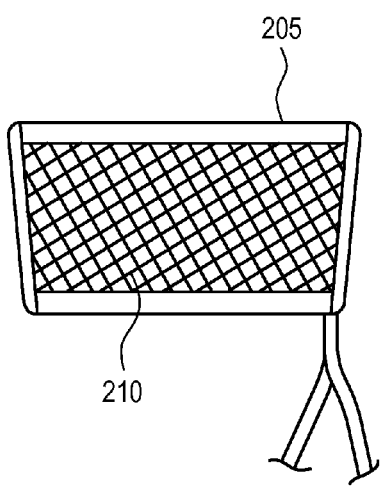

FIGS. 10A-10E are cut-away side views of intra-vaginal devices 205, 405 with various heating elements 210 according to various embodiments of the present invention. The heating element 210 may take various configurations, as shown in cut-away side views in FIGS. 10A-6E. FIG. 10A illustrates a device 405 with an electrical heating element 210 in a serpentine pattern. This pattern allows the device 405 to stretch to some degree to fit a particular individual. Referring briefly to FIGS. 2B and 2C, another embodiment of the device 205 is shown with the heating element 210 in a serpentine pattern. FIG. 10B illustrates a device 205 with an electrical heating element 210 in a helical array. In this embodiment, the heat may be supplied by as little as a single wire positioned around the circumference of the device 205, for example, in an embodiment as depicted in FIG. 6. FIG. 10C illustrates a device 205 with an electrical heating element 210 that is a film, e.g., made of carbon. FIG. 10D illustrates a device 205 with an electrical heating element 210 in a wire mesh pattern. These configurations are merely examples of various configurations the electric heating elements 210 can take; other configurations are within the scope of the present invention.

Figure 10E:
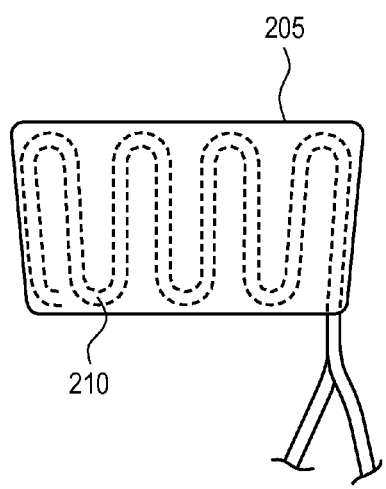

The heating element 210 may include fluid heating. FIG. 10E illustrates a device 205 with a fluid heating element tube 210 in a serpentine pattern. Other configurations for fluid flow are possible, similar to those described in conjunction with the electrical heating embodiments shown in FIGS. 10A-10D. Although FIGS. 10A-10E show the heating element 210 for only a single device 205, 405 configuration, these are merely examples. The various heating elements 210 can be configured in other device 205, 405 shapes.

In another embodiment, the device 205, 405 is heated by an exothermic chemical reaction. In this example, materials encapsulated within the device 205, 405 allow for a chemical reaction that produces the necessary heat.

In yet another embodiment, the device 205, 405 is heated by radio frequency energy transfer. The list of heating methods described herein is not exhaustive, and other technologies for transferring energy to human tissues to raise the temperature of the tissues are within the scope of the present invention.

For the above-described embodiments, the device 205, 405 also may include a means for controlling the effective temperature range of the device, e.g., to ensure that the device temperature is kept in a specific range for safety and effectiveness. For example, for passive heat methods, the device 205, 405 may change colors corresponding to various temperatures. A thermocouple or other feedback device may be incorporated into the device 205, 405 in other embodiments, to provide a readout and facilitate sufficient temperature control. Any number of control technologies, including a failsafe circuit or chip, may be used to provide greater control over the temperature of the device 205, 405.

The heat delivered to the cervix 105 must be warm enough to be effective, but no so hot as to damage the cervical tissues. Thus, the device 205, 405 can operate at a wide range of temperatures. In one embodiment, the device 205, 405 provides heat of a temperature range of 97-120 degrees Fahrenheit. In another embodiment, the device 205, 405 provides heat of a temperature range of 99-106 degrees Fahrenheit. In yet another embodiment, the device 205, 405 provides heat of a temperature range of 100-104 degrees Fahrenheit. These ranges are not intended to be limiting; other temperature ranges are within the scope of the present invention. In one embodiment, therapeutic heat provides for amelioration of discomfort of the cervical region.

Referring again to FIGS. 3A and 3B, in the tampon-based device 305 embodiment and in the internal battery pack embodiment 1100 described in conjunction with FIG. 11 below, electrical supply wires from the heating element 210 may continue down through the secondary ring 310, as depicted in FIG. 3B. The heating element 210 then adjoins with the tampon 320 or battery pack 1105. In the tampon-based device 305, the wires 910 can be either external to the tampon 320 or can be lead through the tampon 320, exiting through the bottom where a retrieval string typically is located.

Figure 11:
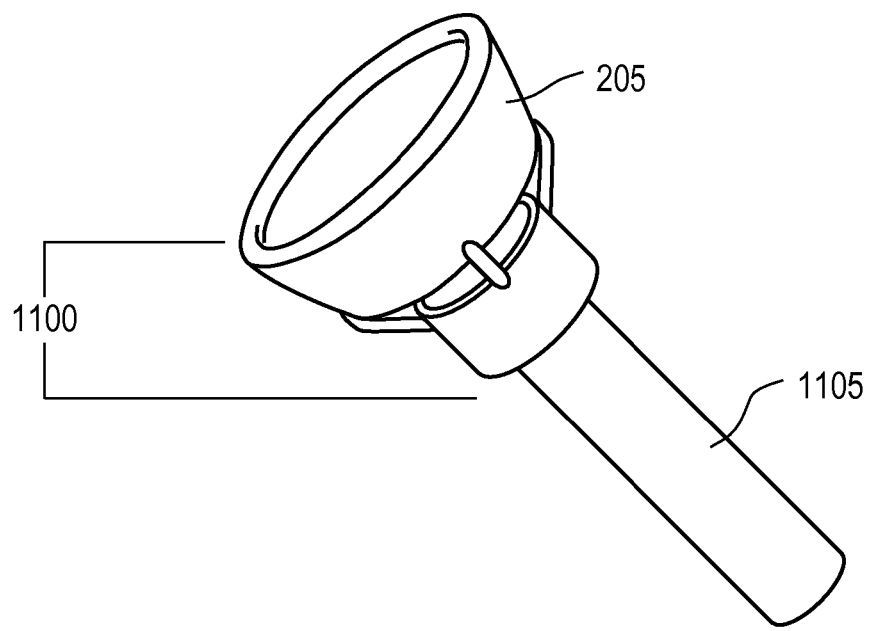
FIG. 11 is a perspective view of an intra-vaginal device with an internal battery pack according to one embodiment of the present invention.

FIG. 11 is a perspective view of an intra-vaginal device 1105 with an internal battery pack according to one embodiment of the present invention. This embodiment of the device 1100 is similar to the tampon based device 305, except that the device 1100 is attached to an internal battery pack 1105 instead of a tampon, as shown in FIG. 11. This embodiment typically would be used when a tampon 320 is not be needed, e.g., for premenstrual cramping, or would be used in combination with an external sanitary napkin. This embodiment allows the device 1100 to be used without external wires 910 or battery pack 915.

Another example of a use of the intra-vaginal devices 205, 405 described herein is for providing therapeutic chemicals to the cervical region. For example, the device 205, 405 is suitable for delivering various drugs and/or hormones to the cervical region by allowing the drugs and/or hormones to leach from the material from which the device is molded. Thus, in one embodiment, the device 205, 405 comprises a material suitable for receiving and retaining a drug and/or hormone for intra-vaginal trans-tissue delivery.

Another example of a use of the intra-vaginal devices 205, 405 described herein is to serve as a barrier type contraceptive device. Thus, this embodiment of the device 405, once in place, is intended to block seminal fluid from entering the os 115 of the cervix 105. The device 405 in this configuration may have addition features, such as a receptacle or reservoir tip for collection of seminal fluid or retention of spermicide.

Yet another example of a use of the intra-vaginal devices 205, 405 described herein is to serve as a device for retention of menstrual fluid. Thus, this embodiment of the device 405, once in place, is intended to block the flow of menstrual fluids out of the cervix 105, e.g. by collecting and retaining the fluid.

Thus, the device 205, 405 and method described herein is configured for delivering therapy of various types to the cervical region, wherein the therapy may be heat therapy, chemical therapy, hormone therapy, contraception, and/or retention of menstrual fluid. In some embodiments, more than one type of therapy may be provided by the device 205, 405, for example heat therapy and retention of menstrual fluid by a device in a closed configuration that also has a heating element.

Insertion and Removal

According to some embodiments, the device 205, 305, 405, 1100 may be inserted digitally. In other embodiments, an insertion device may be used to aid insertion.

Figure 12:
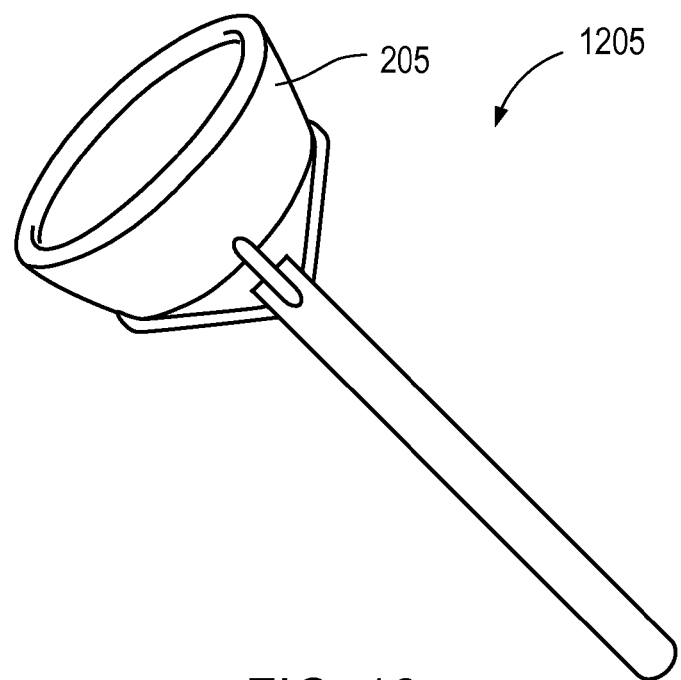
FIG. 12 is a perspective view of an insertion device in conjunction with an intra-vaginal device according to one embodiment of the present invention.

FIG. 12 is a perspective view of an insertion device 1205 in conjunction with an intra-vaginal device 205, 405 according to one embodiment of the present invention. In this example, the insertion device 1205 grasps the intra-vaginal device 205, 405 for insertion into the vaginal canal 107, and then releases the intra-vaginal device 205, 405, e.g., by way of a lever on the insertion device 1205. FIGS. 8A-8C show inserted devices 205, 405.

Figure 13:
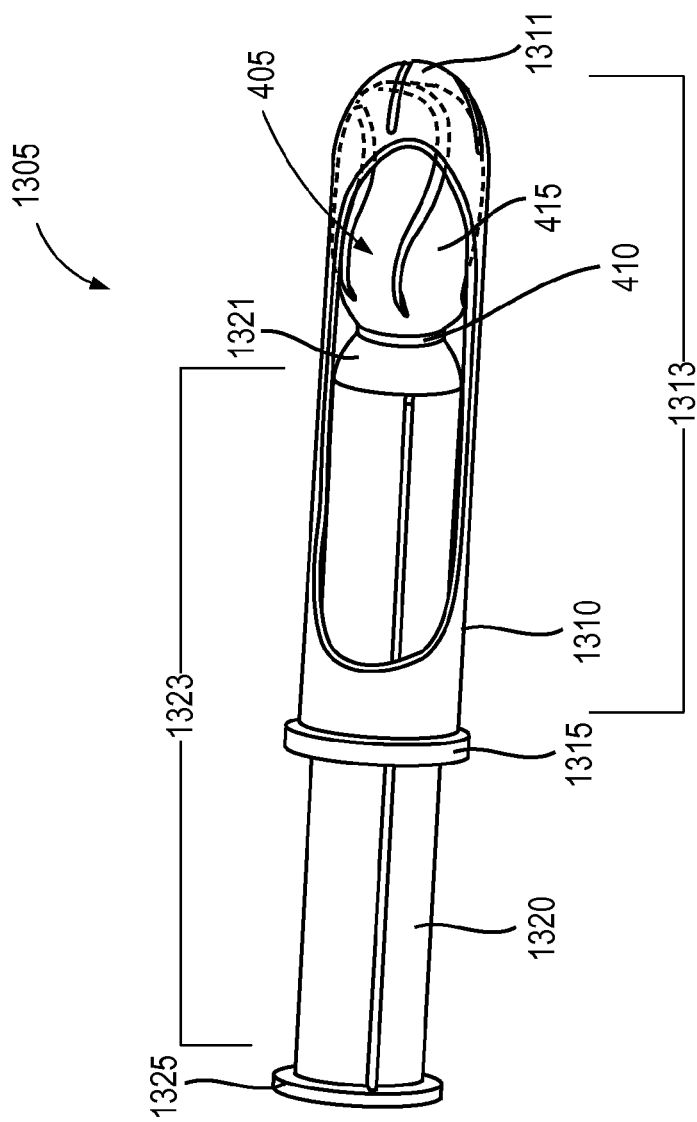
FIG. 13 is a cut-away side view of an intra-vaginal device enclosed in an insertion device according to one embodiment of the present invention.

FIG. 13 is a cut-away side view of an intra-vaginal device 405 enclosed in an insertion device 1305 according to one embodiment of the present invention. The device 405 is shown in its collapsed configuration inside the insertion device 1305. The ring-shaped base 410 and overlapping flaps 415 of the device 405 can be seen. The insertion device 1305 includes a cylindrical outer tube 1310 with an insertion end 1311, a body 1313, and a grip end 1315, and a plunger 1320 with a device end 1321, a body 1323, and a force receiving end 1325. The insertion device 1305 is longer than, but similar in shape to a conventional tampon applicator according to one embodiment. Although the insertion device 1305 is shown with flaps at the insertion end 1311, the insertion device 1305 may not have such flaps according to other embodiments. The plunger 1320 is slideably received inside the cylindrical outer tube 1310, and the device end 1321 of the plunger 1320 has an approximately hemispherical convex tip sized to nestle inside the ring base 410 of the intra-vaginal device 405. The plunger 1320 is designed such that as it expels the device 405 from the tube 1310, it pushes against the center ring 410 of the device 405 and thus allows the device 405 to adjust its angle relative to the plunger 1320 and the alignment of the cervix 105. Thus, the hemispherical tip allows for transfer of the force from the plunger 1320 to the device 405 such that the device 405 pivots into alignment with the cervix uteri 105.

Figure 13A:
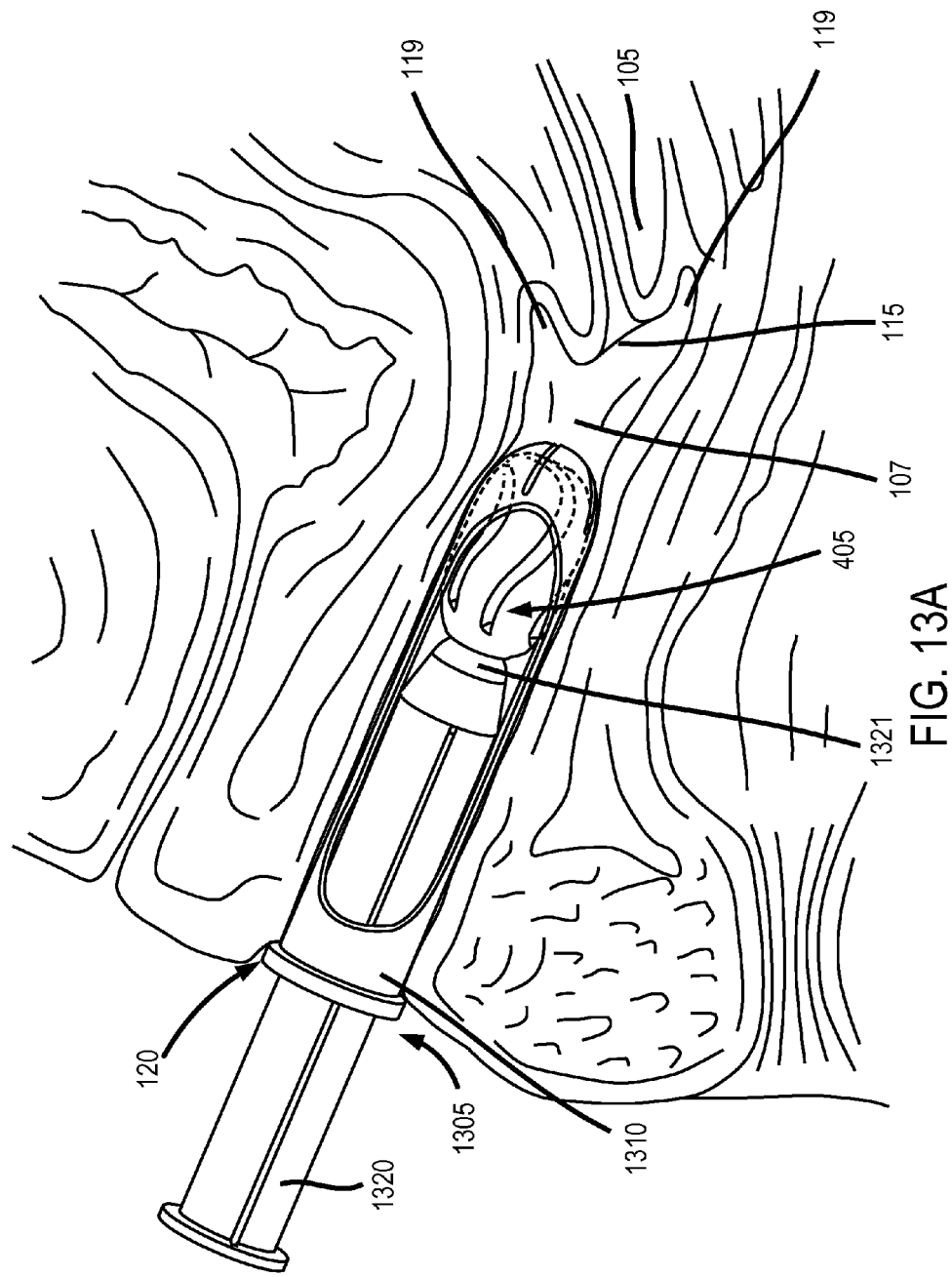
Figure 13C:
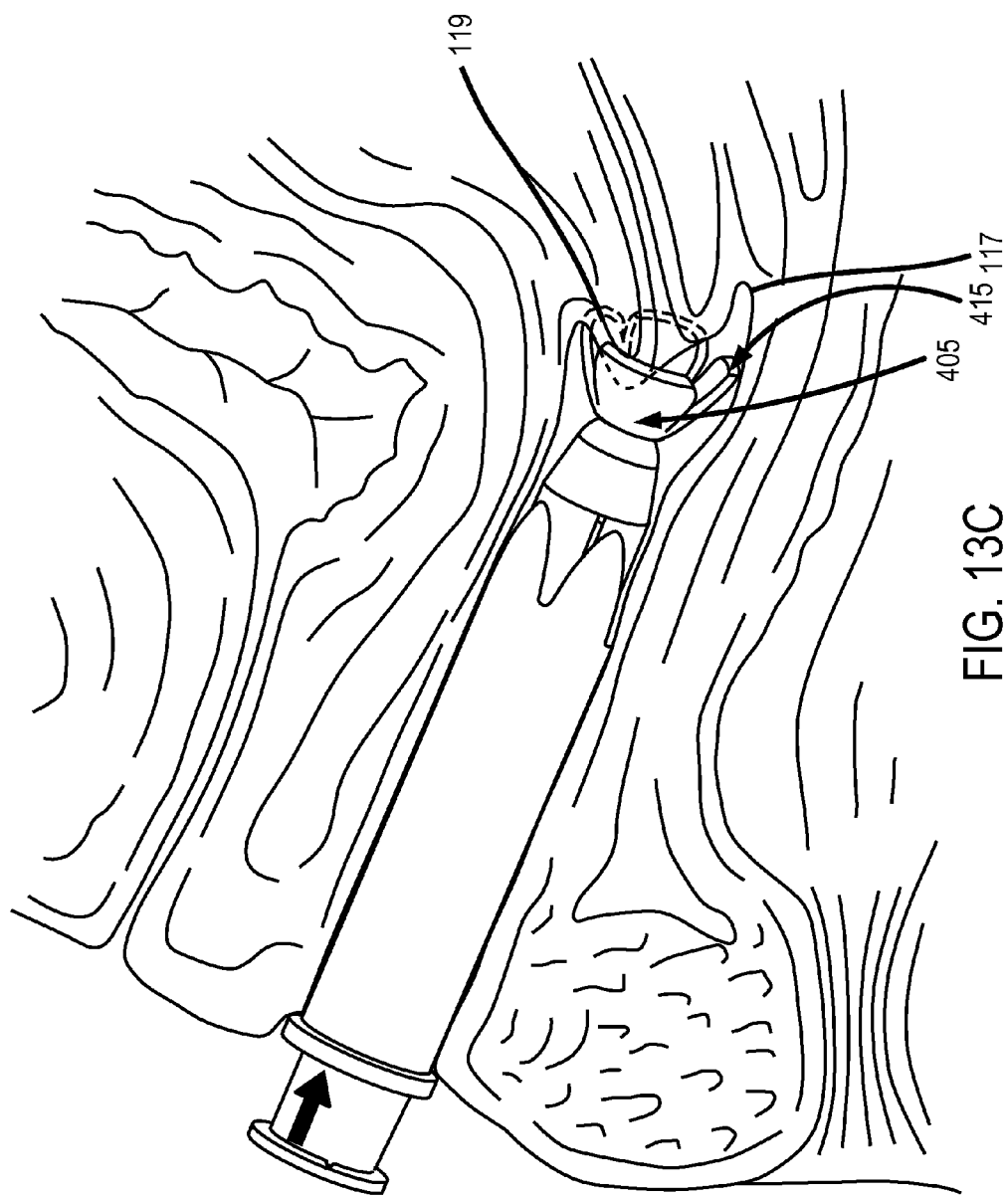
FIGS. 13C-13D are side views of insertion of an intra-vaginal device via an insertion device according to one embodiment of the present invention.
Figure 13D:
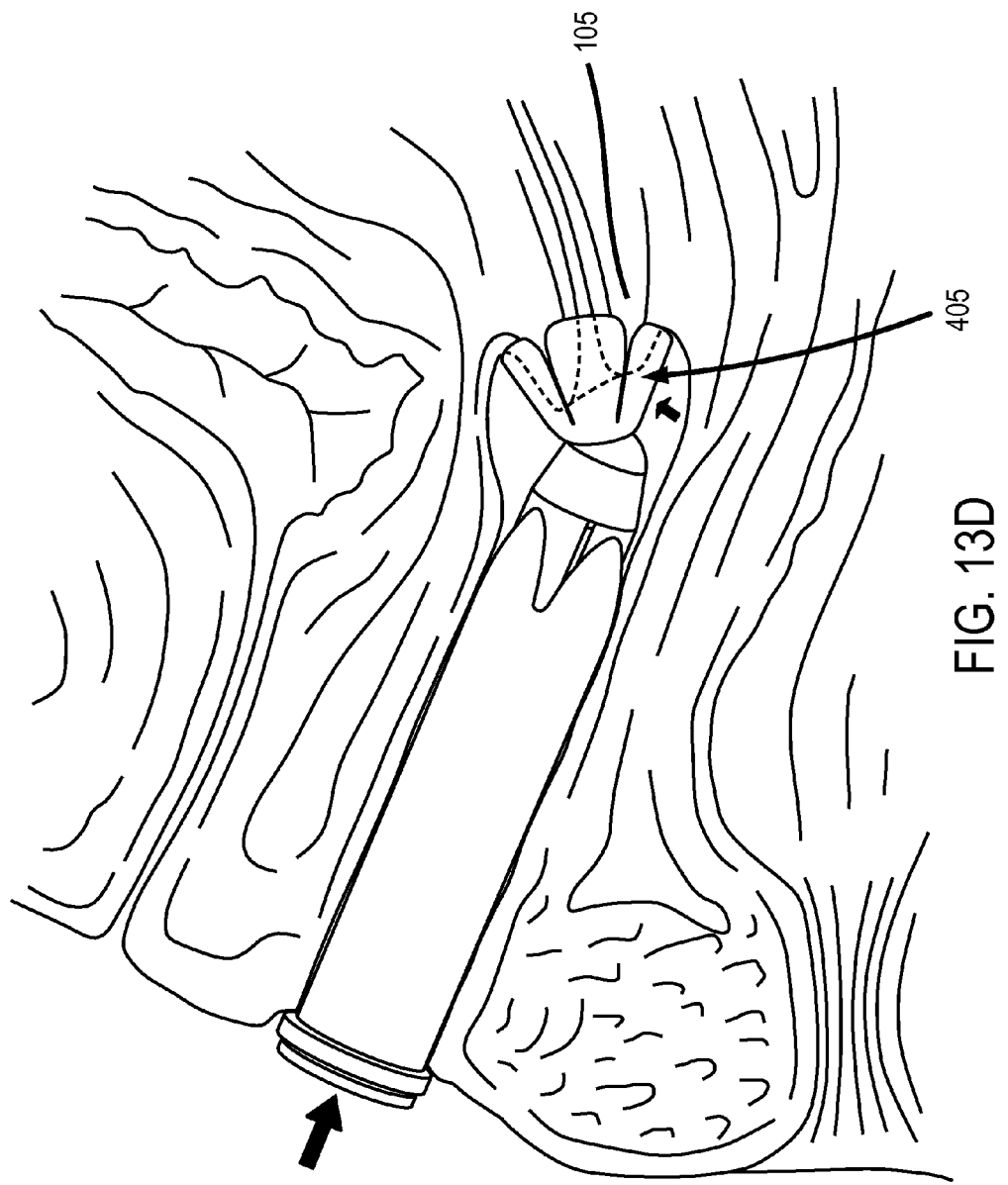
Figure 13E:
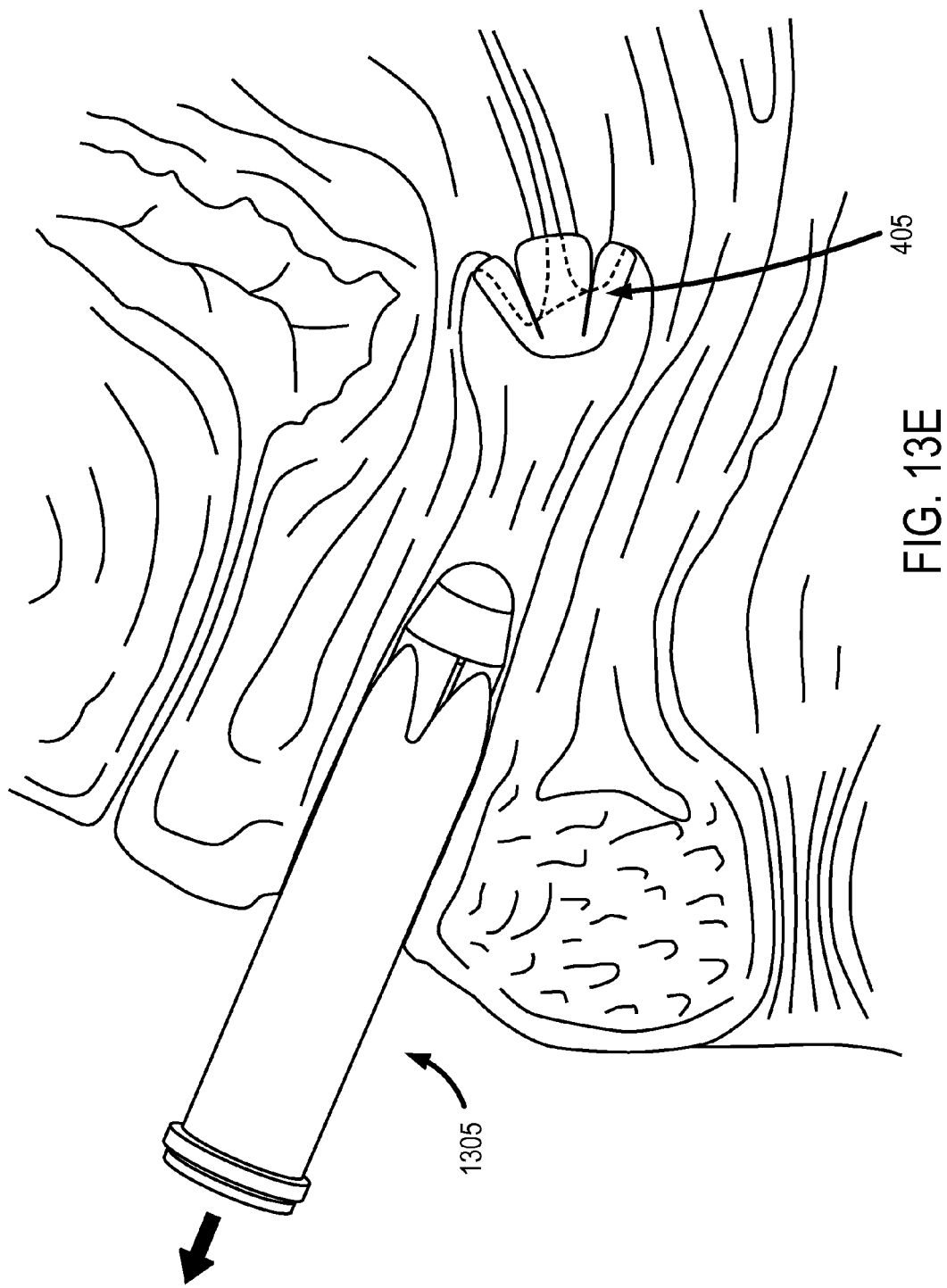
FIG. 13E is a side view of removal of an insertion device according to one embodiment of the present invention.

FIGS. 13A-13B are cut-away side views of insertion of an intra-vaginal device 405 via an insertion device 1305 according to one embodiment of the present invention; FIGS. 13C-13D are side views of insertion of an intra-vaginal device via an insertion device according to one embodiment of the present invention; and FIG. 13E is a side view of removal of an insertion device according to one embodiment of the present invention.

Referring to FIG. 13A, the collapsed device 405 is shown within the insertion device 1305. The plunger 1320 is positioned within the tube 1310 and below the device 405, with the hemispherical tip 1321 of the plunger 1320 engaging the ring base 410 of the device. Because the plunger tip 1321 is larger in diameter than the base 410, it is unable to pass through the ring base 410, and thus can push the device 405 out of the cylindrical outer tube 1310.

FIG. 13A shows the insertion device 1305 having been introduced into the vaginal canal 107 with the intra-vaginal device 405 positioned in a constrained configuration inside the cylindrical outer tube 1310 at the insertion end 1311 of the tube 1310 proximate the device end 1321 of the plunger 1320, positioned for placement of the intra-vaginal device 405 adjacent to the cervix uteri 105.

FIGS. 13B and 13C show the intra-vaginal device 405 being inserted by the insertion device 1305. Upon application of force to the force receiving end 1325 of the plunger 1320, FIG. 13B shows the intra-vaginal device 405 being expelled out of the insertion end 1311 of the cylindrical outer tube 1310. FIG. 13C shows the device 405 having been expelled, expanding into an expanded configuration, causing the flaps 415 to open until they touch the vaginal wall 117.

As the plunger 1320 pushes further with continued application of force, eventually one side of the device 405, i.e., one of the flaps 415, reaches the one of the fornices vaginae 119, as shown in FIG. 13C. Because the side of the device 405 touching a fornix 119 now is prevented from moving further, the axial force placed on the device 405 creates a moment on the device 405, causing the device 405 to pivot, the force being transferred along the hemispherical convex tip 1321 of the plunger 1320 such that the other side of the device 405 contacts a fornix on the opposite side of the cervix 105, as shown in FIG. 13D. Thus, the insertion device 1305 naturally pivots the device 405 into correct alignment with the cervix 105 for its intended therapeutic effect. Referring now to FIG. 13E, the insertion device 1305 is shown being removed, with the intra-vaginal device 405 left in place.

Removal of the device 205, 405 is by means of a retrieval string or tab according to one embodiment. In the embodiment in which the device 405 has overlapping flaps 415, pulling the string moves the device 405 down the vaginal canal 107, and the pressure exerted on the device 405 by the vaginal walls 117 causes the device 405 to change into the collapsed configuration. In the tampon-based configuration, pulling on the tampon string 330 facilitates removal. In embodiments in which wires 910 or tubing 920 lead to the device 205, 405, pulling on the wires may facilitate removal. In other embodiments, other retrieval devices and/or methods may be used to remove the device 205, 405 from the vagina.

Thus, the present invention as shown in the device embodiments described herein allows for highly effective, near continuous relief from dysmenorrhea that is not visible to the casual onlooker. When used during menses as an alternative to tampons, sanitary napkins, or menstrual cups, the present invention allows for longer periods of use, reusability, and avoidance of potential medical risks such as Toxic Shock Syndrome. When used as a barrier birth control method, the present invention limits or avoids the need for medical office fittings for device sizing and simpler and more hygienic use. For the various uses described herein, the device and insertion method of the present invention provides for ease of insertion and correct placement for the desired therapeutic effect.

The present invention has been described in particular detail with respect to one possible embodiment. Those of skill in the art will appreciate that the invention may be practiced in other embodiments. Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

What is claimed is:

1. An intra-vaginal device for placement adjacent to a cervix uteri, the device comprising:
   an approximately circular ring base;
   a plurality of flaps attached to the circumference of the ring base at a first end of the flaps, the flaps adjacent to each other and collectively approximating a hollow inverted frustum with an internal diameter sized to approximately a size of the cervix uteri, wherein a second end of the flaps approximates a top base of the hollow inverted frustum;
   wherein the device is configured to allow the plurality of flaps to overlap over one another so as to decrease an overall diameter of the device for insertion; and
   wherein the plurality of flaps are configured to overlap each other in a spiraling fashion to attain a collapsed configuration that is sufficiently small to permit the device to fit inside a cylindrical tube for insertion.

2. The device of claim 1, wherein the material comprises a hypoallergenic, elastomeric material.

3. The device of claim 1, wherein the ring base is hollow.

4. The device of claim 3, wherein, when the device is in place, the ring base hollow defines an aperture substantially in alignment with the os of the cervix uteri.

5. The device of claim 1, wherein the ring base is solid, and further comprising:
   webbing between each of the flaps such that the flaps collectively form a continuous structure.

6. The device of claim 1, wherein the device is configured for delivering therapy to the cervical region.

7. The device of claim 6, wherein the therapy is selected from the group consisting of: heat therapy, chemical therapy, hormone therapy, contraception, and retention of menstrual fluid.

8. The device of claim 6, wherein the therapy comprises at least two selected from the group consisting of: heat therapy, chemical therapy, hormone therapy, contraception, and retention of menstrual fluid.

9. The apparatus of claim 1, further comprising:
   a placement apparatus for placement of the intravaginal device adjacent to a cervix uteri, the placement apparatus comprising:
     a cylindrical outer tube comprising an insertion end, a body, and a grip end;
     a plunger comprising a device end, a body, and a force receiving end, wherein the plunger is slideably received inside the cylindrical outer tube such that a force applied on the force receiving end of the plunger expels the intra-vaginal device from the cylindrical outer tube at the insertion end; and
     wherein the device end comprises an approximately hemispherical convex tip sized to nestle inside the approximately circular ring base of the intra-vaginal device.

10. The apparatus of 9, wherein the hemispherical tip is configured to allow for transfer of the force from the plunger to the device such that the device pivots into alignment with the cervix uteri.

11. The apparatus of claim 9, wherein the apparatus is configured for introduction into a vaginal canal with the intra-vaginal device positioned in a constrained configuration inside the cylindrical outer tube at the insertion end proximate the device end of the plunger.

12. The apparatus of claim 11, wherein the plunger is configured to expel the intra-vaginal device from the cylindrical outer tube at the insertion end in response to application of a force to the force receiving end of the plunger, wherein the device is configured to change into an expanded configuration upon being expelled, and wherein a first portion of the device, once in the expanded configuration, is configured to contact a first formix, causing the force to be transferred along the hemispherical convex tip such that a second portion of the device contacts a second formix.

13. The apparatus of claim 1, further comprising a heat source associated with the plurality of flaps for providing therapeutic heat to the cervix uteri.

14. The apparatus of claim 1, wherein each of the plurality of flaps is tapered toward an edge to facilitate successive nestling of one flap under an edge of an adjacent flap.

* * * * *